(12) United States Patent
Compadre et al.

(10) Patent No.: US 11,059,800 B2
(45) Date of Patent: Jul. 13, 2021

(54) DEHYDROLEUCODINE DERIVATIVES AND USES THEREOF

(71) Applicants: Bioventures, LLC, Little Rock, AR (US); Universidad Tecnica Particular De Loja, Loja (EC); Cornell University, Ithaca, NY (US)

(72) Inventors: Cesar M. Compadre, Little Rock, AR (US); Paola E. Ordonez, Loja (EC); Monica L. Guzman, Ithaca, NY (US); Darin E. Jones, Little Rock, AR (US); Omar Malagon, Loja (EC); Giovanni Vidari, Loja (EC); Peter Crooks, Little Rock, AR (US)

(73) Assignees: Universidad Tecnica Particular De Loja, Loja (EC); Cornell University, Ithaca, NY (US); BioVentures, LLC, Little Rock, AR (US)

(*) Notice: Subject to any disclaimer, the term of this patent is extended or adjusted under 35 U.S.C. 154(b) by 0 days.

(21) Appl. No.: 16/283,196

(22) Filed: Feb. 22, 2019

(65) Prior Publication Data
US 2019/0185442 A1 Jun. 20, 2019

Related U.S. Application Data

(63) Continuation of application No. 14/903,545, filed as application No. PCT/US2014/046389 on Jul. 11, 2014, now abandoned.

(60) Provisional application No. 61/845,214, filed on Jul. 11, 2013.

(51) Int. Cl.
*C07D 307/93* (2006.01)
*A61K 31/365* (2006.01)
*C07D 307/77* (2006.01)
*C07D 405/06* (2006.01)

(52) U.S. Cl.
CPC .......... *C07D 307/93* (2013.01); *A61K 31/365* (2013.01); *C07D 307/77* (2013.01); *C07D 405/06* (2013.01)

(58) Field of Classification Search
CPC ........ A61K 31/365; A61P 35/00; A61P 35/02; C07D 307/77; C07D 307/93; C07D 405/06
USPC ....................................................... 514/232
See application file for complete search history.

(56) References Cited

U.S. PATENT DOCUMENTS

| | | |
|---|---|---|
| 6,693,127 B1 | 2/2004 | Adekenov |
| 6,908,630 B2 | 6/2005 | Babish et al. |
| 9,255,078 B2 * | 2/2016 | Chen .................... C07D 307/93 |
| 10,463,644 B2 * | 11/2019 | Chen ................... A61K 31/5377 |
| 2010/0196889 A1 | 8/2010 | Bankaitis-Davis et al. |
| 2012/0122943 A1 * | 5/2012 | Crooks ................ C07D 493/04 514/387 |
| 2013/0109749 A1 | 5/2013 | Chen et al. |
| 2016/0176839 A1 | 6/2016 | Compadre et al. |

FOREIGN PATENT DOCUMENTS

| | | |
|---|---|---|
| WO | 2012145678 A1 | 10/2012 |
| WO | 2015006715 A1 | 1/2015 |

OTHER PUBLICATIONS

Paola E. Ordóñez (Journal of Natural Products 2016 79 (4), 691-696 DOI: 10.1021/acs.jnatprod.5b00383 (Dehydroleucodine, a Sesquiterpene Lactone from Gynoxys verrucosa, Demonstrates Cytotoxic Activity against Human Leukemia Cells).*
Hou, Xueling et al (AN: 2012:242278, HCAPLUS, DN: 156:311239;CN 102351823, Jul. 28, 2011 Title: Lactucin derivatives, their preparation method and application as antitumor drugs).*
Adekenov, S., "Synthesis of New Derivatives of Natural Guaianolides," Chemistry of Natural Compounds, 2013, pp. 988-995, vol. 48, No. 6, Springer Science+Business Media, New York.
Arantes, F. et al., "A quantum chemical and chemometric study of sesquiterpene lactones with cytotoxicity against tumor cells," J. Chemometrics, 2011, pp. 401-407, vol. 25, John Wiley & Sons, Ltd.
Compound Summary for CID 57509311, PubChem, Aug. 8, 2012, 3 pgs.
Compound Summary for CID 57509311, PubChem, Dec. 10, 2016, 9 pgs.
Costantino, V. et al., "The Sesquiterpene Lactone Dehydroleucodine Triggers Senescence and Apoptosis in Association with Accumulation of DNA Damage Markers," PLoS One, Jan. 2013, pp. 1-15, vol. 8, Issue 1, e53168.
Extended European Search Report dated Jan. 2, 2017 from related European Patent Application No. 14823619.3; 10 pgs.
Ghantous, A. et al., "What made sesquiterpene lactones reach cancer clinical trials?," Drug Discovery Today, Aug. 2010, pp. 668-678, vol. 15, Nos. 15/16, Elsevier.
Guzman, M. et al., "The sesquiterpene lactone parthenolide induces apoptosis of human acute myelogenous leukemia stem and progenitor cells," Blood, Jun. 1, 2005, pp. 4163-4169, vol. 105, No. 11.
Huang, S. et al., "Blockade of NF-[kappa]B activity in human prostate cancer cells is associated with suppression of angiogenesis, invasion, and metastasis," Oncogene, 2001, pp. 4188-4197, vol. 20, Nature Publishing Group.
International Search Report and Written Opinion dated Oct. 16, 2014 from related International Patent Application No. PCT/US2014/046389; 14 pgs.
Koehne, C-H. et al., "COX-2 Inhibition and Colorectal Cancer," Seminars in Oncology, Apr. 2004, pp. 12-21, vol. 31, No. 2, Suppl. 7, Elsevier Inc.
Nakagawa, Y. et al., "A potent apoptosis-inducing activity of a sesquiterpene lactone, arucanoline, in HL60 cells: a crucial role of apoptosis-inducing factor," J. Pharmacol. Sci., 2005, pp. 242-252, vol. 97.

(Continued)

*Primary Examiner* — Sabiha N Qazi
(74) *Attorney, Agent, or Firm* — Polsinelli PC

(57) ABSTRACT

The present invention provides dehydroleucodine derivatives. In particular, the present invention provides amine derivatives of dehydroleucodine and methods of using dehydroleucodine and the amine derivatives of dehydroleucodine to inhibit the growth of cancer cells.

9 Claims, 13 Drawing Sheets

(56) References Cited

OTHER PUBLICATIONS

Office Action dated Oct. 7, 2016 from related U.S. Appl. No. 14/903,545; 7 pgs.
Office Action dated Feb. 2, 2017 from related U.S. Appl. No. 14/903,545; 8 pgs.
Office Action dated Apr. 6, 2017 from related U.S. Appl. No. 14/903,545; 8 pgs.
Office Action dated May 26, 2017 from related U.S. Appl. No. 14/903,545; 9 pgs.
Office Action dated Mar. 14, 2018 from related U.S. Appl. No. 14/903,545; 8 pgs.
Office Action dated Oct. 23, 2018 from related U.S. Appl. No. 14/903,545; 8 pgs.
Liu, X. et al., "Inhibition of Cyclooxygenase-2 Suppresses Angiogenesis and the Growth of Prostate Cancer In Vivo," J. Urology, Sep. 2000, pp. 820-825, vol. 164.
Priestap, H. et al., "Dehydroleucodine and dehydroparishin-B inhibit proliferation and motility of B16 melanoma cells," Phytochem. Lett., 2012, pp. 581-585, vol. 5, Elsevier B.V.
Sarma, S. et al., "Induction of apoptosis in human leukemia cells through the production of reactive oxygen species and activation of HMOX1 and Noxa by benzene, toluene, and o-xylene," Toxicology, 2011, pp. 109-117, vol. 280, Elsevier Ireland Ltd.
Sartor, T. et al., "The Sesquiterpene Lactone Dehydroleucodine Reversibly Inhibits Allium cepa L. Root Growth," Biocell, 2001, pp. 29-34, vol. 25, No. 1.
Setia, R. et al., "Chemical modifications of dehydrocostus lactone from Saussurea lappa and the study of structure-activity relationship," Indian Journal of Chemistry, May 2007, pp. 847-851, vol. 46B.
Shao, J. et al., "Overexpression of the wild-type p53 gene inhibits NF-[kappa]B activity and synergizes with aspirin to nduce apoptosis in human colon cancer cells," Oncogene, Feb. 10, 2000, pp. 726-736, vol. 19, No. 6, Macmillan Publishers Ltd.
Wendel, G. et al., "Effect of Dehydroleucodine in Experimental Colitis in Rats and Mice," Pharmacol. Res., 1999, pp. 339-344, vol. 40, No. 4.
Yim, M-S. et al., "HMOX1 is an Important Prognostic Indicator of Nonmuscle Invasive Bladder Cancer Recurrence and Progression," J. Urology, Feb. 2011, pp. 701-705, vol. 185.
Zhang, Q. et al., "Guaianolide Sesquiterpene Lactones, a Source to Discover Agents That Selectively Inhibit Acute Myelogenous Leukemia Stem and Progenitor Cells," J. Med. Chem., 2012, pp. 8757-8769, vol. 55.

\* cited by examiner

A

B

DEHYDROLEUCODINE DERIVATIVES AND USES THEREOF

CROSS REFERENCE TO RELATED APPLICATIONS

This application is a continuation of U.S. application Ser. No. 14/903,545, filed Jan. 7, 2016 and claims the benefit of PCT Application PCT/US2014/046389, filed Jul. 11, 2014, which claims the benefit of U.S. provisional application No. 61/845,214, filed Jul. 11, 2013, each of the disclosures of which are hereby incorporated by reference in its entirety.

GOVERNMENTAL RIGHTS

This invention was made with government support under 1 DP2 OD007399-01 awarded by the National Institutes of Health. The government has certain rights in the invention.

FIELD OF THE INVENTION

The present disclosure relates to the use of dehydroleucodine and to the use and preparation of dehydroleucodine derivatives for the treatment of various types of cancers including: colon cancer, CNS cancer, melanoma, prostate cancer, acute lymphoblastic leukemia, chronic lymphocytic leukemia, acute myelogenous leukemia, chronic myeloid leukemia, and cutaneous T cell leukemia (CTCL).

BACKGROUND OF THE INVENTION

Many species of higher plants are used for healthcare purposes and a large number of the current anticancer drugs originate from natural sources. Given the wide variety of biologically active natural compounds and their wide structural diversity, it may be worthwhile to continue screening plants for compounds that could be useful as chemotherapeutic agents. Sesquiterpene lactones constitute a large and diverse group of biologically active plant chemicals that have been identified in several plant families. Some sesquiterpene lactones possess anti-inflammatory and/or antitumor activity. For example, parthenolide is highly cytotoxic, and a derivative of parthenolide is being tested in clinical trials as an anticancer agent. Parthenolide, however, has poor solubility and bioavailability, thus limiting its clinical use. There is a need, therefore, for new water-soluble compounds with robust cytotoxic anticancer properties.

SUMMARY OF THE INVENTION

Among the various aspects of the present disclosure is the provision of amino derivatives of dehydroleucodine. One aspect of the disclosure encompasses a compound comprising Formula (I) or a pharmaceutically acceptable salt thereof:

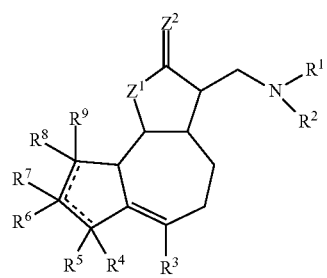

(I)

wherein:
$R^1$ and $R^2$ are independently hydrogen, hydrocarbyl, or substituted hydrocarbyl, or $R^1$ and $R^2$ together form an optionally substituted, saturated or unsaturated, carbocyclic or heterocyclic ring or ring system;
$R^3$ is hydrogen, hydroxy, amine, cyano, halo, nitro, phospho, sulfo, thiol, hydrocarbyl, or substituted hydrocarbyl;
$R^4$, $R^5$, $R^6$, $R^7$, $R^8$, and $R^9$ are independently hydrogen, hydroxy, amine, cyano, halo, nitro, phospho, sulfo, thiol, hydrocarbyl, or substituted hydrocarbyl; or any pair of $R^4$ and $R^5$, $R^6$ and $R^7$, or $R^8$ and $R^9$ together form $=$O, $=$S, $=$CH$_2$, or $=$NR$^a$, wherein $R^a$ is hydrogen, hydrocarbyl, or substituted hydrocarbyl;
$Z^1$ and $Z^2$ are independently oxygen, sulfur, nitrogen, or CH$_2$; and
----- is a single or double bond.

Another aspect of the present disclosure provides a method for inhibiting growth of a cancer cell. The method comprises contacting the cancer cell with an amount of a compound comprising Formula (I), or a pharmaceutically acceptable salt thereof, effective to inhibit growth of the cancer cell. The compound comprising Formula (I):

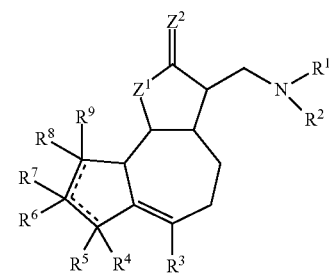

(I)

wherein:
$R^1$ and $R^2$ are independently hydrogen, hydrocarbyl, or substituted hydrocarbyl, or $R^1$ and $R^2$ together form an optionally substituted, saturated or unsaturated, carbocyclic or heterocyclic ring or ring system;
$R^3$ is hydrogen, hydroxy, amine, cyano, halo, nitro, phospho, sulfo, thiol, hydrocarbyl, or substituted hydrocarbyl;
$R^4$, $R^5$, $R^6$, $R^7$, $R^8$, and $R^9$ are independently hydrogen, hydroxy, amine, cyano, halo, nitro, phospho, sulfo, thiol, hydrocarbyl, or substituted hydrocarbyl; or
any pair of $R^4$ and $R^5$, $R^6$ and $R^7$, or $R^8$ and $R^9$ together form $=$O, $=$S, $=$CH$_2$, or $=$NR$^a$, wherein $R^a$ is hydrogen, hydrocarbyl, or substituted hydrocarbyl;
$Z^1$ and $Z^2$ are independently oxygen, sulfur, nitrogen, or CH$_2$; and
----- is a single or double bond.

Another aspect of the present disclosure provides a method for inhibiting growth of a cancer cell. The method comprises contacting the cancer cell with an amount of dehydroleucodine, or a pharmaceutically acceptable salt thereof, effective to inhibit growth of the cancer cell.

Other aspects and iterations of the disclosure are described in more detail below.

BRIEF DESCRIPTION OF THE DRAWINGS

The application file contains at least one drawing executed in color. Copies of this patent application publication with color drawing(s) will be provided by the Office upon request and payment of the necessary fee.

FIG. 1A shows the expression of Hmox1 in KG1 cells. FIG. 1B plots the expression of HSPA1A in KG1 cells. FIG. 1C presents the expression of HSPH1 in KG1 cells. FIG. 1D shows the expression of Hmox1 in MOLM13 cells. FIG. 1E presents the expression of HSPH1 in MOLM13 cells. Error bars represent S.E.M.

(FIG. 7A) Viability of normal cells after treatment with DHL and its derivatives. Bone marrow and peripheral blood mononuclear cells were isolated from healthy donors and treated for 48 hours with 20 μM DHL or PTL, or 50 μM Leucodine, DHL-Morpholine, DHL-Proline, or DHL-Piperidine. Cells were also treated with 10 μg/mL G. Verrucosa extract as a reference. Viability was assessed by Annexin V and 7AAD staining using flow cytometry. Each line represents a distinct sample, with viabilities calculated relative to an untreated control. (FIG. 7B) Average viability of AML cell lines compared to normal BM/PBMNCs with 20 μM DHL treatment after 48 hours. The viabilities of all 8 cell lines from Table 5 at 20 μM DHL were averaged and graphed next to the average viability of the 4 healthy samples from FIG. 7A. The significance between the two groups was calculated using the Mann-Whitney test, p=0.004.

(FIG. 8A) Graphical representation of the fold changes of HMOX-1 in MOLM-13 cells. Cells were seeded at 0.5 million cells per milliliter and subject to 20 μM of DHL, leucodine, DHL-proline, DHL-piperidine, DHL-morpholine, or parthenolide for 6 hours. RNA was then extracted and quantitative PCR was performed. Experiments were performed in triplicates. Lines represent mean for each specimen, with error bars representing the SD. Fold change was calculated by the delta-delta Ct method. (FIG. 8B) Graphical representation of the fold changes of HSPA1A in MOLM-13, with the same experimental setup and analysis as FIG. 7A. (FIG. 8C) Graphical representation of the fold changes of NF-κB in MOLM-13, with the same experimental setup and analysis as FIG. 7A. (FIG. 8D) Immunoblot for MOLM-13 cells after 6 hours of treatment with either DHL or PTL with 10 or 20 μM. Blot was probed for phospho-p65 and p65 antibodies. Total p65 is shown as the loading control.

(FIG. 9A) Graphical representation of the fold changes of HMOX-1 in MV-411 cells. Cells were seeded at 0.5 million cells per milliliter and subject to 20 μM of DHL, leucodine, DHL-proline, DHL-piperidine, DHL-morpholine, or parthenolide for 6 hours. RNA was then extracted and quantitative PCR was performed. Experiments were performed in triplicates. Lines represent mean for each specimen, with error bars representing the SD. Fold change was calculated by the delta-delta Ct method. (FIG. 9B) Graphical representation of the fold changes of HSPA1A in MV-411 cells, with the same experimental setup and analysis as FIG. 7A.

DETAILED DESCRIPTION OF THE INVENTION

Figure 1:
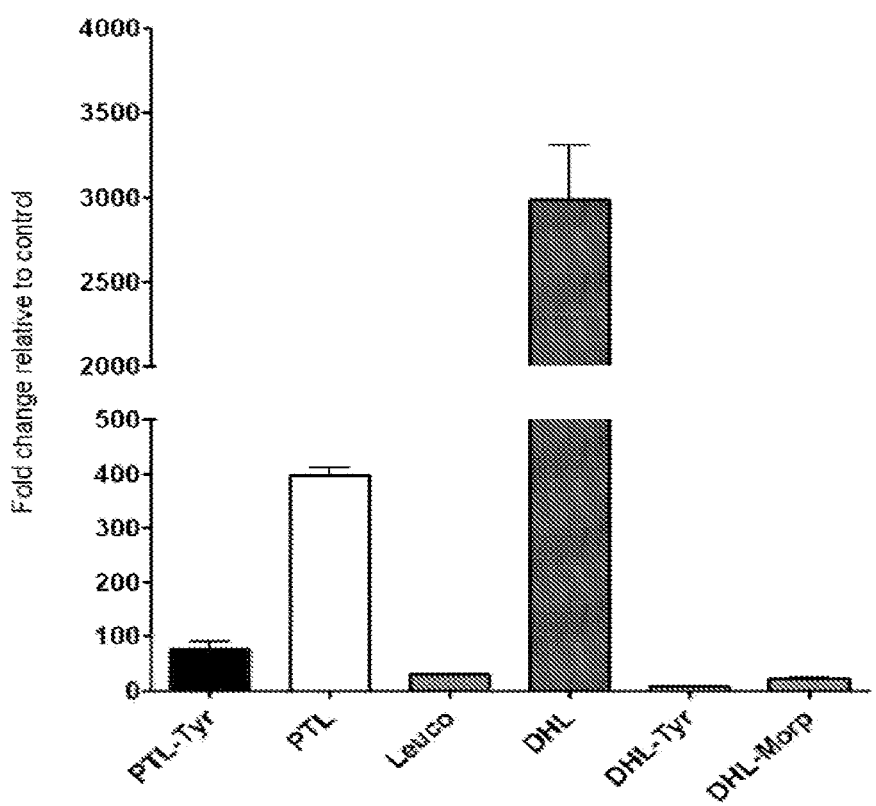
FIG. 1A, FIG. 1B, FIG. 1C, FIG. 1D and FIG. 1E present the changes in gene expression in KG1 or MOLM13 cells after exposure to dehydroleucodine, parthenolide, or derivatives thereof. Plotted is the fold change in expression relative to control after treatment with parthenolide-tyramine (PTL-Tyr), parthenolide (PTL), leucodine (Leuco), dehydroleucodine (DHL), dehydroleucodine-tyramine (DHL-Tyr), or dehydroleucodine-morpholine (DHL-Morp).
Figure 1:
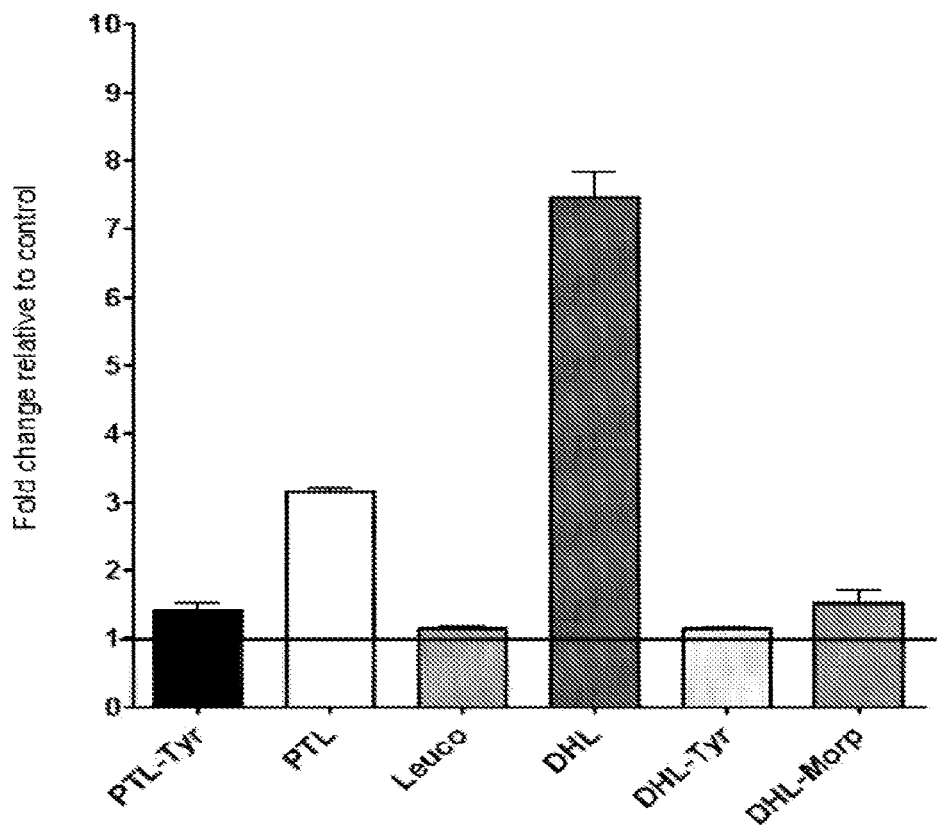
Figure 1:
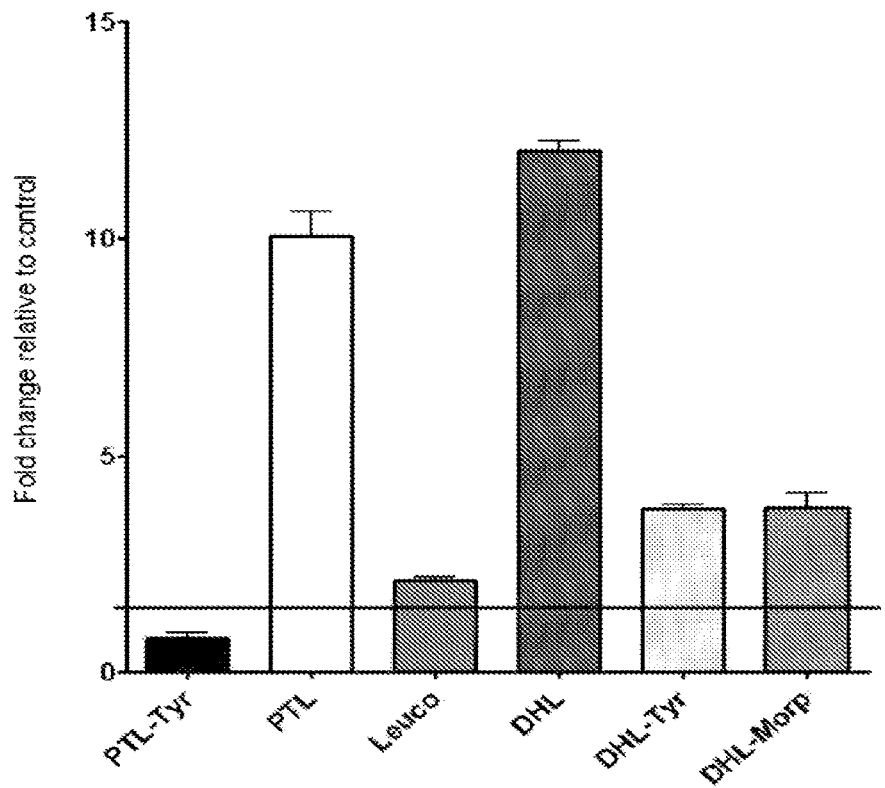
Figure 1:
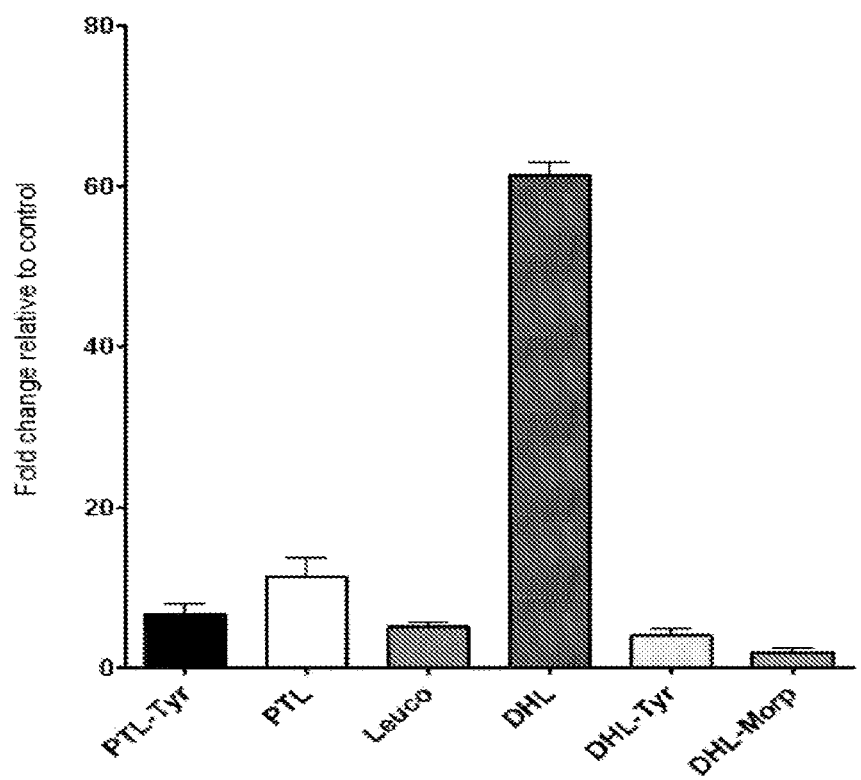

Provided herein are derivatives of dehydroleucodine. Primary among the various substituents, is the replacement of the α-methylene group of the γ-lactone ring with an amine moiety. The amine derivatives of dehydroleucodine have improved water solubility relative to dehydroleucodine. Importantly, the amine derivatives of dehydroleucodine have anticancer activity. Also provided herein are methods of using dehydroleucodine or derivatives of dehydroleucodine to inhibit the growth, proliferation, and metastasis of cancer cells. Dehydroleucodine or derivatives of dehydroleucodine, therefore, may be used to treat leukemias, colon, prostate, melanoma, central nervous system and other cancers, including multi-drug resistant cancers.

(I) Compounds Comprising Formula (I)

One aspect of the present disclosure provides a compound comprising Formula (I) or a pharmaceutically acceptable salt thereof:

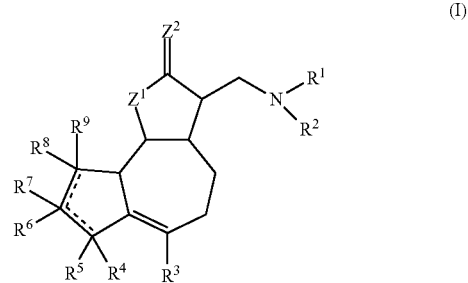

wherein:
R¹ and R² are independently hydrogen, hydrocarbyl, or substituted hydrocarbyl, or R¹ and R² together form an optionally substituted, saturated or unsaturated, carbocyclic or heterocyclic ring or ring system;
R³ is hydrogen, hydroxy, amine, cyano, halo, nitro, phospho, sulfo, thiol, hydrocarbyl, or substituted hydrocarbyl;
R⁴, R⁵, R⁶, R⁷, R⁸, and R⁹ are independently hydrogen, hydroxy, amine, cyano, halo, nitro, phospho, sulfo, thiol, hydrocarbyl, or substituted hydrocarbyl; or
any pair of R⁴ and R⁵, R⁶ and R⁷, or R⁸ and R⁹ together form =O, =S, =CH₂, or =NRᵃ, wherein Rᵃ is hydrogen, hydrocarbyl, or substituted hydrocarbyl;
Z¹ and Z² are independently oxygen, sulfur, nitrogen, or CH₂; and
===== is a single or double bond.

In some embodiments, R¹ and R² independently may be hydrogen, alkyl, substituted alkyl, heterocyclic, substituted heterocyclic, alkenyl, substituted alkenyl, alkynyl, substituted alkynyl, aryl, substituted aryl, heteroaryl, substituted heteroaryl, or R¹ and R² together may form a heterocylic, substituted heterocyclic, heteroaryl, or substituted heteroaryl ring or ring system. In one embodiment, R¹ and R² independently may be hydrogen, alkyl, substituted alkyl, cycloalkyl, haloalkyl, alkoxy, hydroxyalkyl, alkenyl, substituted alkenyl, alkynyl, substituted alkynyl, aryl, substituted aryl, arylalkyl, heterocyclic, substituted heterocyclic, heteroaryl, substituted heteroaryl, carbonylalkyl, carbonyl substituted alkyl, carbonylaryl, carbonylalkoxy, carbonylaryl, carbonylaryloxy, carbonylaminoalkyl, or carbonylaminoaryl. In another embodiment, R¹ and R² together may form —CH₂(CH₂)ₙCH₂— where n is 0 to 5; and together with N form an optionally substituted ring, wherein the ring may be optionally fused to a cycloalkyl or aryl group to form a bicyclic or tricyclic system, and said system may be optionally substituted and/or optionally comprising one or more heteroatoms. In still another embodiment, R¹ and R² together may form —CH₂(CH₂)ₙCH₂Y—; where Y is O, S, Se, Si, P, —CO—, —SO—, —SO₂—, or —PO—; and n is 0 to 5; and together with N form an optionally substituted ring, wherein the ring may be optionally fused to a cycloalkyl or aryl group to form a bicyclic or tricyclic ring system, and said system may be optionally substituted and/or optionally comprising one or more heteroatoms. In a further embodiment, R¹ and R² together may form —(CH₂)ₐ—Y—(CH₂)ᵦ—; where Y is O, S, Se, Si, P, —CO—, —SO—, —SO₂—, or —PO—; and a and b are independently 1 to 4; and together with N form an optionally substituted ring, wherein the ring may be optionally fused to a cycloalkyl or aryl group to form a bicyclic or tricyclic ring system, and said system may be optionally substituted and/or optionally comprising one or more heteroatoms. In still another embodiment, R¹ and R² together with N may form an optionally substituted ring or ring system chosen from aziridinyl, azetidinyl, pyrrolidinyl, piperidynyl, heptamethyleneiminyl, hexamethyleneiminyl, imidazolyl, indolyl, morpholinyl, oxazinyl, piperazinyl, prolinyl, purinyl, pyrazolyl, pyrimidinyl, pyrrolyl, quinolinyl, quinuclidinyl, thiazolyl, or triazinyl.

In one embodiment, Z¹ may be oxygen and Z² may be CH₂. In still another embodiment, Z¹ may be nitrogen and Z² may be oxygen. In yet another embodiment, Z¹ may be sulfur and Z² may be oxygen. In a further embodiment, both Z¹ and Z² may be oxygen.

In another embodiment, the compound comprising Formula (I) may comprise Formula (Ia):

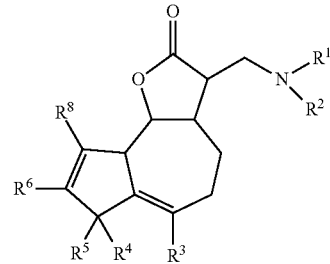

(Ia)

wherein:
R¹ and R² are as described above;
R³, R⁶, and R⁸ are independently hydrogen, hydroxy, amine, cyano, halo, nitro, phospho, sulfo, thiol, hydrocarbyl, or substituted hydrocarbyl; and
R⁴ and R⁵ are independently hydrogen, hydroxy, amine, cyano, halo, nitro, phospho, sulfo, thiol, hydrocarbyl, or substituted hydrocarbyl, or R⁴ and R⁵ together form =O, =S, =CH₂, or =NRᵃ, wherein Rᵃ is hydrogen, hydrocarbyl, or substituted hydrocarbyl.

In certain embodiments, R³, R⁵, R⁶, and R⁸ independently may be hydrogen, hydroxy, alkyl, substituted alkyl, hydroxyalkyl, alkyloxy, amino, or aminoalkyl. In one embodiment, R³ and R⁸ may be $C_1$-$C_6$ alkyl, and R⁵ and R⁶ may be hydrogen. In a further embodiment, R³ and R⁸ may be methyl, and R⁵ and R⁶ may be hydrogen. In additional embodiments, R⁴ may be —XRᵇ, wherein X is —O—, —NH—, —S—, —SO—, —SO₂—, —CO—, —CO₂— and Rᵇ is hydrogen, alkyl, substituted alkyl, haloalkyl, alkoxy, hydroxyalkyl, cycloalkyl, substituted cycloalkyl, heterocycloalkyl, substituted heterocycloalkyl, alkenyl, substituted alkenyl, alkynyl, substituted alkynyl, aryl, substituted aryl, arylalkyl, heteroaryl, substituted heteroaryl, carbonylaminoalkyl, carbonylamino substituted alkyl, carbonylaminoaryl, or carbonylamino substituted aryl.

In a further embodiment, the compound comprising Formula (I) may comprise Formula (Ib):

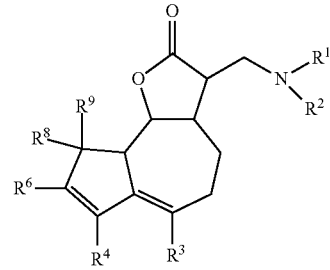

(Ib)

wherein:
R¹ and R² are as described above;
R³, R⁴, and R⁶ are independently hydrogen, hydroxy, amine, cyano, halo, nitro, phospho, sulfo, thiol, hydrocarbyl, or substituted hydrocarbyl; and
R⁸ and R⁹ are independently are independently hydrogen, hydroxy, amine, cyano, halo, nitro, phospho, sulfo, thiol, hydrocarbyl, or substituted hydrocarbyl, or R⁸ and R⁹ together form =O, =S, =CH₂, or =NRᵃ, wherein Rᵃ is hydrogen, hydrocarbyl, or substituted hydrocarbyl.

In various embodiments, $R^3$, $R^4$, $R^6$, and $R^8$ independently may be hydrogen, hydroxy, alkyl, substituted alkyl, hydroxyalkyl, alkyloxy, amino, or aminoalkyl. In one embodiment, $R^3$ may be $C_1$-$C_6$ alkyl, $R^4$ and $R^6$ may be hydrogen, and $R^8$ may be $C_1$-$C_6$ alkyl. In a further embodiment, $R^3$ and $R^8$ may be methyl, and $R^4$ and $R^6$ may be hydrogen. In further embodiments, $R^9$ may be $R^9$ may be —$XR^c$, wherein X is —O—, —NH—, —S—, —SO—, —$SO_2$—, —CO—, —$CO_2$— and $R^c$ is hydrogen, alkyl, substituted alkyl, hydroxyalkyl, alkenyl, substituted alkenyl, alkynyl, or substituted alkynyl.

In still another embodiment, the compound comprising Formula (I) may comprise Formula (Ic):

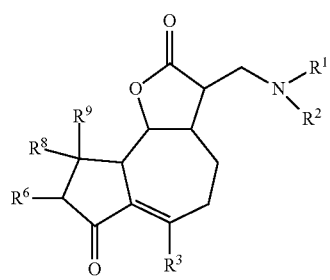

(Ic)

wherein:

$R^1$ and $R^2$ are as described above;

$R^3$ and $R^6$ are independently hydrogen, hydroxy, amine, cyano, halo, nitro, phospho, sulfo, thiol, hydrocarbyl, or substituted hydrocarbyl; and $R^8$ and $R^9$ are independently are independently hydrogen, hydroxy, amine, cyano, halo, nitro, phospho, sulfo, thiol, hydrocarbyl, or substituted hydrocarbyl, or $R^8$ and $R^9$ together form =O, =S, =$CH_2$, or =$NR^a$, wherein $R^a$ is hydrogen, hydrocarbyl, or substituted hydrocarbyl.

In certain embodiments, $R^3$, $R^6$, and $R^8$ independently may be hydrogen, hydroxy, alkyl, substituted alkyl, hydroxyalkyl, alkyloxy, amino, or aminoalkyl. In some embodiments, $R^3$ may be $C_1$-$C_6$ alkyl, $R^6$ may be hydrogen or hydroxy, and $R^8$ may be $C_1$-$C_6$ alkyl. In other embodiments, $R^3$ and $R^8$ may be methyl, and $R^6$ may be hydrogen or hydroxy. In additional embodiments, $R^9$ may be hydrogen, alkyl, substituted alkyl, cycloalkyl, haloalkyl, alkoxy, aminoalkyl, hydroxyalkyl, sulfoxyalkyl, sulfonylalkyl, thioalkyl, heterocyclic, substituted heterocyclic, alkenyl, substituted alkenyl, alkynyl, substituted alkynyl, aryl, substituted aryl, arylalkyl, aryloxy, aminoaryl, thioaryl, sulfoxyaryl, sulfonylaryl, heteroaryl, substituted heteroaryl, cyano, carboxy, alkylcarboxylate, aryl carboxylate, carboxamide, N-alkyl carboxamide, N-aryl carboxamide, N,N-dialkyl carboxamide, N,N-diaryl carboxamide, N-alky N-aryl carboxamide, carbonyl aminoalkyl, carbonylamino substituted alkyl, carbonylaminoaryl, carbonylamino substituted aryl, carbonylalkoxy, or carbonylaryloxy.

In yet another embodiment, the compound comprising Formula (I) may comprise Formula (Id):

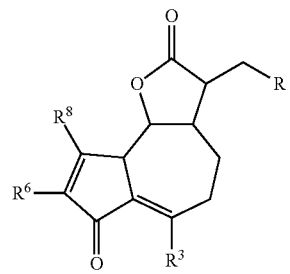

(Id)

wherein:

R is N-hydrocarbyl or N-substituted hydrocarbyl; and $R^3$, $R^6$, and $R^8$ are independently hydrogen, hydroxy, amine, cyano, halo, nitro, phospho, sulfo, thiol, hydrocarbyl, or substituted hydrocarbyl.

In various embodiments, R may be N-alkyl, N-cycloalkyl, N-alkenyl, N-alkynyl, N-aryl, N-substituted alkyl, N-substituted cycloalkyl, N-substituted alkenyl, N-substituted alkynyl, or N-substituted aryl. In certain embodiments, R may be prolinyl, pipridinyl, morpholinyl, tyraminyl, aziridinyl, azetidinyl, pyrrolidinyl, piperidynyl, heptamethyleneiminyl, hexamethyleneiminyl, imidazolyl, indolyl, morpholinyl, oxazinyl, piperazinyl, purinyl, pyrazolyl, pyrimidinyl, pyrrolyl, quinolinyl, quinuclidinyl, thiazolyl, or triazinyl. In some embodiments, $R^3$, $R^6$, and $R^8$ independently may be hydrogen, hydroxy, alkyl, substituted alkyl, hydroxyalkyl, alkyloxy, amino, or aminoalkyl. In one embodiment, $R^3$ may be $C_1$-$C_6$ alkyl, $R^6$ may be hydrogen, and $R^8$ may be $C_1$-$C_6$ alkyl. In another embodiment, $R^3$ and $R^8$ may be methyl, and $R^6$ may be hydrogen.

The compounds comprising Formula (I) can exist in tautomeric, geometric, or stereoisomeric forms. For example, the carbons at certain positions may be stereogenic (or chiral). The compound comprising Formula (I) may have The compounds comprising Formulas (I), (Ia), (Ib), (Ic), or (Id) can exist in tautomeric, geometric, or stereoisomeric forms. For example, the carbons at certain positions may be stereogenic (or chiral). At each chiral center, the stereochemistry at the carbon atom is independently R or S. The compound comprising Formula (I) can have chiral carbons at the positions indicated below with asterisks:

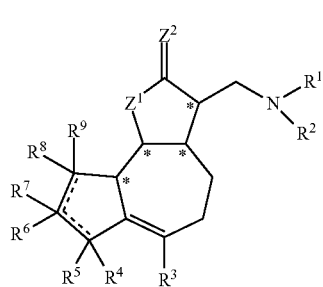

(I)

The configuration of the indicated four carbons may be RRRR, RRRS, RRSR, RSRR, SRRR, RRSS, RSSR, SSRR, SRRS, SRSR, RSRS, RSSS, SRSS, SSRS, SSSR, or SSSS.

The compounds comprising Formulas (I), (Ia), (Ib), (Ic), and (Id) disclosed herein may be in the form of free bases or pharmaceutically acceptable salts thereof. The term "pharmaceutically acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds disclosed herein may be prepared from inorganic acids or organic acids. Non-limiting examples of suitable inorganic acids include hydrochloric, hydrobromic, hydroiodic, nitric, carbonic, sulfuric, perchloric, and phosphoric acid. Appropriate organic acids may be selected from aliphatic, cycloaliphatic, aromatic, araliphatic, heterocyclic, carboxylic and sulfonic classes of organic acids, examples of which are formic, acetic, oxalic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts of compounds disclosed herein include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine), and procaine. All of these salts may be prepared by conventional means from the corresponding compound by reacting, for example, the appropriate acid or base with the any of the compounds disclosed herein.

The compounds disclosed herein may be prepared by a variety of methods. For example, N-derived substituents may be added to the lactone moiety by contacting dehydroleucodine or a derivative thereof comprising the α-methylene-γ-lactone moiety with a secondary amine in the presence of a suitable solvent (e.g., triethylamine). The reaction mixture may be incubated at a temperature from about 10-40° C. for a period of time ranging from several hours to several days. Substituents at other positions may be added using well known chemical synthesis procedures.

(II) Method for Producing a Compound Comprising Formula (I)

In another embodiment, the disclosure provides a method of making the compound comprising Formula (I). The method comprises contacting a compound comprising Formula (II) with an amine in the presence of a proton acceptor. The compound of Formula (II) comprises:

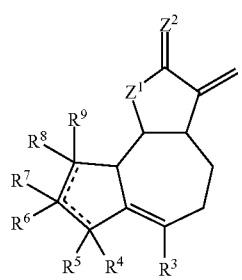

(II)

wherein, $R^3$, $R^4$, $R^5$, $R^6$, $R^7$, $R^8$, $R^9$, $Z^1$ and $Z^2$ may be chosen as described in section (I).

The compound comprising Formula (II) is a dehydroleucodine or a derivative of dehydroleucodine. The process of making a compound comprising Formula (I) may involve the replacement of the α-methylene group of the γ-lactone ring with an amine moiety.

The method comprises contacting the compound comprising Formula (II) with an amine. The amine may be a primary amine (i.e., $NH_2R'$, wherein R' is alkyl or aryl) or a secondary amine (i.e., NHR'R", wherein R' and R" independently are alkyl or aryl). In some embodiments, the secondary amine may be a cyclic amine. Non-limiting examples of suitable amines include proline, piperidine, morpholine, tyramine methylamine, ethylamine, propylamine, isopropylamine, ethanolamine, aniline, dimethylamine, methylethanolamine, diphenylamine, aziridine, azetidine, pyrrolidine, heptamethyleneimine, hexamethyleneimine, imidazole, indole, oxazine, piperazine, purine, pyrazole, pyrimidine, pyrrole, quinoline, quinuclidine, thiazole, and triazine. In specific embodiments, the amine may include proline, piperidine, morpholine, or tyramine.

The mole to mole ratio of the compound comprising Formula (II) to the amine can and will range depending upon the identity of the amine and/or the compound of Formula (II). In general, the mole to mole ratio of the compound comprising Formula (II) to the amine varies from about 1:1 to about 1:40. In some embodiments, the mole to mole ratio of the compound comprising Formula (II) to the amine may range from about 1:10 to about 1:30. In some other embodiments, the mole to mole ratio of the compound comprising Formula (II) to the amine may range from 1:10 to 1:30. In various embodiments, the mole to mole ratio of the compound comprising Formula (II) to the amine is about 1:10, about 1:15, about 1:20, about 1:25 or about 1:30. In various other embodiments, the mole to mole ratio of the compound comprising Formula (II) to the amine is 1:10, 1:15, 1:20, 1:25 or 1:30. In an exemplary embodiment, the mole to mole ratio of the compound comprising Formula (II) to the amine is 1:20.

The reaction generally is carried out in the presence of a solvent. Typically, the solvent is an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In exemplary embodiments, one of the solvents is an alcohol solvent. In one specific embodiment, one of the solvents is ethanol.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In one specific embodiment, the proton acceptor is triethylamine. The amount of proton acceptor included in the reaction can and will vary, but can be readily determined by a person of ordinary skill in the art.

The amount of time over which the reaction is conducted may also vary within different embodiments. In some embodiments, the reaction may be conducted over a period of 2 hours to 24 hours. In particular embodiments, the reaction is carried out for about 8 hours, about 9 hours, about 10 hours, about 11 hours, about 12 hours, about 13 hours, about 14 hours, about 15 hours, about 16 hours, about 17 hours, about 18 hours, about 19 hours or about 20 hours. In other embodiments, the reaction is carried out for 8 hours, 9 hours, 10 hours, 11 hours, 12 hours, 13 hours, 14 hours, 15 hours, 16 hours, 17 hours, 18 hours, 19 hours or 20 hours. In specific embodiments, the reaction is conducted for about 14 hours to about 18 hours. In other specific embodiments, the reaction is conducted for 14 hours to 18 hours.

The temperature may vary over different embodiments, in some embodiments the temperature may range from about 20° C. to about 80° C. In particular embodiments the temperature may range from about 20° C. to about 30° C., from about 30° C. to about 40° C., from about 40° C. to about 50° C., from about 50° C. to about 60° C., from about 60° C. to about 70° C., or from about 70° C. to about 80° C. In other particular embodiments the temperature may range from 20° C. to 30° C., from 30° C. to 40° C., from 40° C. to 50° C., from 50° C. to 60° C., from 60° C. to 70° C., or from 70° C. to 80° C. In specific embodiments, the temperature may range from about 20° C. to about 30° C. In other specific embodiments, the temperature may range from 20° C. to 30° C.

The synthesized compounds may be used in their crude form or they may be purified. The compounds may be purified by any suitable method known in the art including through column chromatography, crystallization, distillation, extraction, and the like. In one preferred embodiment, the compounds are recrystallized from a solvent.

(III) Compositions

The present disclosure also provides pharmaceutical compositions. The pharmaceutical composition comprises a compound comprising Formulas (I), (Ia), (Ib), (Ic), or (d), which are detailed above in section (I), as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising DHL or a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compund of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N- methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional goups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(IV) Methods for Inhibiting Cancer Cell Growth

A further aspect of the present disclosure provides a method for inhibiting growth of a cancer cell. Cancer cell growth includes cell proliferation and cell metastasis. The method comprises contacting the cancer cell with an effective amount of a compound comprising Formulas (I), (Ia), (Ib), (Ic), or (Id), or a pharmaceutically acceptable salt thereof, wherein the amount is effective to inhibit growth of the cancer cell. Compounds comprising Formulas (I), (Ia), (Ib), (Ic), and (Id) are detailed above in section (I). In some embodiments, the compound comprising Formulas (I), (Ia), (Ib), (Ic), or (Id) is used as part of a composition, examples of which are detailed above in section (III).

In another embodiment, the method comprises contacting the cancer cell with an effective amount of dehydroleucodine or a pharmaceutically acceptable salt thereof, wherein the amount is effective to inhibit growth of the cancer cell. In some embodiments, dehydroleucodine is used as part of a composition, examples of which are detailed above in section (III).

(a) Contacting the Cell

In some embodiments, the cancer cell may be in vitro. The cancer cell may be an established, commercially-available cancer cell line (e.g., American Type Culture Collection (ATCC), Manassas, Va.). The cancer cell line may be derived from a blood cancer or a solid tumor. The cancer cell line may be a human cell line or a mammalian cell line. In a specific embodiment, the cancer cell line may be derived from a blood cancer. In one exemplary embodiment, the cancer cell line may be derived from a leukemic cell. The leukemic cell may be an acute myeloid leukemia cell, a chronic myeloid leukemia cell, an acute lymphocytic leukemia cell, a chronic lymphocytic leukemia cell, a cutaneous T cell leukemia, or another type of leukemia cell. In some embodiments, the cancer cell line may be a leukemia cell line such as Kasumi-1, KCL22, KG-1, MV4-11, MOLM-13, TF-1, THP-1, TUR, HL-60, U937, CCRF-CEM, K-562 or RPMI-8226. In other embodiments, the cancer cell line may be a hematopoietic or lymphoid cell line. Non-limiting examples of hematopoietic or lymphoid cell lines include 380, 697, A3-KAW, A3/KAW, A4-Fuk, A4/Fuk, ALL-PO, ALL-SIL, AML-193, AMO-1, ARH-77, ATN-1, BALL-1, BC-3, BCP-1, BDCM, BE-13, BL-41, BL-70, BV-173, C8166, CA46, CCRF-CEM, CI-1, CMK, CMK-11-5, CMK-86, CML-T1, COLO 775, COLO-677, CTB-1, CTV-1, Daudi, DB, DEL, DG-75, DND-41, DOHH-2, EB1, EB2, EHEB, EJM, EM-2, EOL-1, EoL-1-cell, F-36P, GA-10, GA-10-Clone-4, GDM-1, GR-ST, GRANTA-519, H9, HAL-01, HD-MY-Z, HDLM-2, HEL, HEL 92.1.7, HH, HL-60, HPB-ALL, Hs 604.T, Hs 611.T, Hs 616.T, Hs 751.T, HT, HTK-, HuNS1, HuT 102, HuT 78, IM-9, J-RT3-T3-5, JeKo-1, JiyoyeP-2003, JJN-3, JK-1, JM1, JURKAT, JURL-MK1, JVM-2, JVM-3, K-562, K052, KARPAS-299, KAR-PAS-422, KARPAS-45, KARPAS-620, KASUMI-1, KASUMI-2, Kasumi-6, KCL-22, KE-37, KE-97, KG-1, KHM-1B, Ki-JK, KM-H2, KMM-1, KMOE-2, KMS-11, KMS-12-BM, KMS-12-PE, KMS-18, KMS-20, KMS-21BM, KMS-26, KMS-27, KMS-28BM, KMS-34, KO52, KOPN-8, KU812, KY821, KYO-1, L-1236, L-363, L-428, L-540, LAMA-84, LC4-1, Loucy, LOUCY, LP-1, M-07e, MC-CAR, MC116, ME-1, MEC-1, MEC-2, MEG-01, MHH-CALL-2, MHH-CALL-3, MHH-CALL-4, MHH-PREB-1, Mino, MJ, ML-2, MLMA, MM1-S, MN-60, MOLM-13, MOLM-16, MOLM-6, MOLP-2, MOLP-8, MOLT-13, MOLT-16, MOLT-4, MONO-MAC-1, MONO-MAC-6, MOTN-1, MUTZ-1, MUTZ-3, MUTZ-5, MV-4-11, NALM-1, NALM-19, NALM-6, NAMALWA, NB-4, NCI-H929, NCO2, NKM-1, NOMO-1, NU-DHL-1, NU-DUL-1, OCI-AML2, OCI-AML3, OCI-AML5, OCI-LY-19, OCI-LY10, OCI-LY3, OCI-M1, OPM-2, P12-ICHIKAWA, P30-OHK, P31-FUJ, P31/FUJ, P3HR-1, PCM6, PEER, PF-382, Pfeiffer, PL-21, Raji, Ramos-2G6-4C10, RCH-ACV, REC-1, Reh, REH, RI-1, RL, RPMI 8226, RPMI-8226, RPMI-8402, RS4-11, "RS4; 11", SEM, Set-2, SIG-M5, SK-MM-2, SKM-1, SR, SR-786, ST486, SU-DHL-1, SU-DHL-10, SU-DHL-4, SU-DHL-5, SU-DHL-6, SU-DHL-8, SUP-B15, SUP-B8, SUP-HD1, SUP-M2, SUP-T1, SUP-T11, TALL-1, TF-1, THP-1, TO 175.T, Toledo, TUR, U-266, U-698-M, U-937, U266B1, UT-7, WSU-DLCL2, and WSU-NHL.

In another exemplary embodiment, the cancer cell line may be derived from a solid tumor cell. The solid tumor cell may be a colon cancer cell, a prostate cancer cell, a central nervous system cancer cell, a melanoma cell, or another type of solid tumor cell. In a specific embodiment, the solid tumor cell may be a colon cancer cell, a prostate cancer cell, or a central nervous system (CNS) cancer cell. In some embodiments, the cancer cell line may be a human solid tumor cell line such as HCT-116, SW-620, SNB-75, U251, PC-3, or DU-145. In other embodiments, the cancer cell line may be any colon cancer cell line. Non-limiting examples of colon cancer cell lines include C2BBe1, CaR-1, CCK-81, CL-11, CL-14, CL-34, CL-40, CoCM-1, COLO 201, COLO 205, COLO-205, COLO-320, COLO-320-HSR, COLO-678, COLO-741, CW-2, DLD-1, GP2d, GP5d, HCC-56, HCC2998, HCT 116, HCT-116, HCT-15, HCT-8, HRT-18, Hs 255.T, Hs 675.T, Hs 698.T, HT-29, HT115, HT55, KM12, LoVo, LS 180, LS-1034, LS-123, LS-174T, LS-411N, LS-513, LS1034, LS123, LS411N, LS513, MDST8, NCI-H508, NCI-H630, NCI-H716, NCI-H747, OUMS-23, RCM-1, RKO, SK-CO-1, SNU-1033, SNU-1040, SNU-1197, SNU-175, SNU-283, SNU-407, SNU-503, SNU-61, SNU-81, SNU-C1, SNU-C2A, SNU-C2B, SNU-C4, SNU-C5, SW1116, SW1417, SW1463, SW403, SW48, SW480, SW620, SW837, SW948, and T84. In still other embodiments, the cancer cell line may be any prostate cancer cell line. Non-limiting examples of prostate cancer cell lines include 22Rv1, 22RV1, DU 145, DU-145, LNCaP, clone FGC, LNCaP-Clone-FGC, MDA PCa 2b, NCI-H660, PC-3, PrEC LH, and VCaP. In still other embodiments, the cancer cell line may be any central nervous system cancer cell line. Non-limiting examples of central nervous system cancer cell lines include 1321N1, 42-MG-BA, 8-MG-BA, A1207, A172, AM-38, Becker, CAS-1, CCF-STTG1, CH-157MN, D-245MG, D-247MG, D-263MG, D-336MG, D-392MG, D-397MG, D-423MG, D-502MG, D-538MG, D-542MG, D-566MG, D283 Med, D341 Med, Daoy, DBTRG-05MG, DK-MG, F5, GAMG, GB-1, GI-1, GMS-10, GOS-3, H4, Hs 683, IOMM-Lee, KALS-1, KG-1-C, KINGS-1, KNS-42, KNS-60, KNS-81, KNS-81-FD, KS-1, LN-18, LN-215, LN-229, LN-235, LN-319, LN-340, LN-405, LN-428, LN-443, LN-464, LN382, LNZ308, M059J, M059K, MOG-G-CCM, MOG-G-UVW, NMC-G1, no-10, no-11, ONS-76, PFSK-1, SF-172, SF-295, SF126, SF268, SF295, SF539, SF767, SK-MG-1, SNB-19, SNB19, SNB75, SNU-1105, SNU-201, SNU-466, SNU-489, SNU-626, SNU-738, SW 1088, SW 1783, SW1088, SW1783, T98G, TM-31, U-118 MG, U-118-MG, U-138 MG, U-178, U-251 MG, U-87 MG, U-87-MG, U251, U343, YH-13, YKG-1, and YKG1.

In other embodiments, the cancer cell may be in vivo; i.e., the cell may be disposed in a subject. In such embodiments, the cancer cell is contacted with the compound comprising Formula (I) by administering the compound comprising Formula (I) to the subject. In another embodiment, the cancer cell is contacted with dehydroleucodine by administering dehydroleucodine to the subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer cell disposed in the subject may be a blood cancer cell (e.g., leukemia, lymphoma, myeloma) or a solid tumor cancer cell. The cancer may be primary or metastatic; early stage or late stage; and/or the tumor may be malignant or benign. Non-limiting cancers include bladder cancer, bone cancer, brain cancer, breast cancer, central nervous system cancer, cervical cancer, colon cancer, colorectal cancer, duodenal cancer, endometrial cancer, esophageal cancer, eye cancer, gallbladder cancer, germ cell cancer, kidney cancer, larynx cancer, leukemia, liver cancer, lymphoma, lung cancer, melanoma, mouth/throat cancer, ovarian cancer, pancreatic cancer, prostate cancer, skin cancer, testicular cancer, thyroid cancer, vaginal cancer, and drug resistant cancers. In one exemplary embodiment, the cancer cell may be a leukemia. The leukemia may be an acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia. In another exemplary embodiment, the cancer cell may be a colon cancer. In still another exemplary embodiment, the cancer cell may be a prostate cancer. In still yet another exemplary embodiment, the cancer cell may be a CNS cancer. DHL may be especially useful in CNS cancer because of its experimentally determined Log P octanol/water of 2.33 (±0.16) that is close to the optimum to penetrate the blood-brain barrier (Log P=2)

Dehydroleucodine or the compound comprising Formulas (I), (Ia), (Ib), (Ic), or (Id) may be administered to the subject orally (as a solid or a liquid), parenterally (which includes intramuscular, intravenous, intradermal, intraperitoneal, and subcutaneous), or topically (which includes transmucosal and transdermal). An effective amount of the compound can be determined by a skilled practitioner in view of desired dosages and potential side effects of the compound.

Dehydroleucodine or the compound comprising Formulas (I), (Ia), (Ib), (Ic), or (Id) may be administered once or administered repeatedly to the subject. Repeated administrations may be at regular intervals of 2 hours, 6 hours, 12 hours, 24 hours, 2 days, 5 days, 7 days, 30 days, and so forth.

(b) Inhibiting Cancer Cell Growth

Following contact with an effective amount of the compound comprising Formulas (I), (Ia), (Ib), (Ic), or (Id), growth of the cancer cell is inhibited. Additionally, following contact with an effective amount of dehydroleucodine, growth of the cancer cell is inhibited. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators.

In an embodiment, contact with an effective amount of the compound comprising Formulas (I), (Ia), (Ib), (Ic), or (Id) selectively inhibits growth of cancer cells. As such, a compound comprising Formulas (I), (Ia), (Ib), (Ic), or (Id) does not appreciably kill non-cancer cells at the same concentration. Accordingly, more than 50% of non-cancer cells remain viable following contact with a compound comprising Formulas (I), (Ia), (Ib), (Ic), or (Id) at the same concentration. For example about 50%, about 55%, about 60%, about 65%, about 70%, about 75%, about 80%, about 85%, about 90%, about 95% or about 100% of non-cancer cells remain viable following contact with a compound comprising Formulas (I), (Ia), (Ib), (Ic), or (Id) at the same concentration. Or, 50%, 55%, 60%, 65%, 70%, 75%, 80%, 85%, 90%, 95% or 100% of non-cancer cells remain viable following contact with a compound comprising Formulas (I), (Ia), (Ib), (Ic), or (Id) at the same concentration.

In another embodiment, contact with an effective amount of dehydroleucodine selectively inhibits growth of cancer cells. As such, dehydroleucodine does not appreciably kill non-cancer cells at the same concentration. Accordingly, more than 50% of non-cancer cells remain viable following contact with dehydroleucodine at the same concentration. For example about 50%, about 55%, about 60%, about 65%, about 70%, about 75%, about 80%, about 85%, about 90%, about 95% or about 100% of non-cancer cells remain viable following contact with dehydroleucodine at the same concentration. Or, 50%, 55%, 60%, 65%, 70%, 75%, 80%, 85%, 90%, 95% or 100% of non-cancer cells remain viable following contact with dehydroleucodine at the same concentration.

In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be cancer cell growth in a sample that has not been contacted with dehydroleucodine or a compound comprising Formulas (I), (Ia), (Ib), (Ic), or (Id). In another example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of dehydroleucodine or a compound comprising Formulas (I), (Ia), (Ib), (Ic), or (Id), a reference sample may be a sample obtained from a subject before therapy or administration of dehydroleucodine or the compound comprising Formulas (I), (Ia), (Ib), (Ic), or (Id) began.

In an embodiment, contact with an effective amount of the compound comprising Formulas (I), (Ia), (Ib), (Ic), or (Id) inhibits activation of NF-κB. In another embodiment, contact with an effective amount of dehydroleucodine inhibits activation of NF-κB. Inhibition of activation of NF-κB may induce apoptosis. As such, the inhibition of activation of NF-κB may be measured in vitro using standard cell viability or cell cytotoxicity assays in combination with cell counting methods as described above. Or, the inhibition of activation of NF-κB may be measured in vivo using imaging procedures and/or molecular diagnostic indicators. Inhibition of activation of NF-κB may also be measured by measuring nucleic acid expression of NF-κB. Methods to measure nucleic acid expression are known in the art and may include PCR, quantitative PCR, RT-PCR, qRT-PCR, microarray or array.

In various embodiments, expression of NF-κB may be reduced about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. Any suitable reference value known in the art may be used. For example, a suitable reference value may be the expression of NF-κB in a sample that has not been contacted with dehydroleucodine or a compound comprising Formulas (I), (Ia), (Ib), (Ic), or (Id). In another example, a suitable reference value may be the expression of NF-κB in a subject, or group of subjects, of the same species that has no clinically detectable symptom of cancer. In another example, a suitable reference value may be expression of NF-κB in a subject, or group of subjects, of the same species that has no clinically detectable cancer. In another example, a suitable reference value may be the background signal of the assay as determined by methods known in the art. In another example, a suitable reference value may be a measurement of the expression of NF-κB in a reference sample obtained from the same subject. The reference sample may be obtained from a subject when the subject had no clinically detectable symptom of cancer. A skilled artisan will appreciate that it is not always possible or desirable to obtain a reference sample from a subject when the subject is otherwise healthy. For example, when monitoring the effectiveness of a therapy or efficacy of dehydroleucodine or a compound comprising Formulas (I), (Ia), (Ib), (Ic), or (Id), a reference sample may be a sample obtained from a subject before therapy or administration of dehydroleucodine or the compound comprising Formulas (I), (Ia), (Ib), (Ic), or (Id) began. In an additional example, a suitable reference sample may be from an individual or group of individuals that has been shown not to have cancer.

In another embodiment, contact with an effective amount of the compound comprising Formulas (I), (Ia), (Ib), (Ic), or (Id) induces oxidative stress. Alternatively, contact with an effective amount of dehydroleucodine induces oxidative stress. Induction of oxidative stress may result in cell death, apoptosis and/or necrosis. As such, the induction of oxidative stress may be measured in vitro using standard cell viability or cell cytotoxicity assays in combination with cell counting methods as described above. Or, the induction of oxidative stress may be measured in vivo using imaging procedures and/or molecular diagnostic indicators. Induction of oxidative stress may also be measured by measuring nucleic acid expression of markers of oxidative stress. A skilled artisan would be able to markers of oxidative stress. In an exemplary embodiment markers of oxidative stress may be, but not limited to, HMOX1, HSPA1A and HSPH1. As such, induction of oxidative stress may be measured by measuring nucleic acid expression of HMOX1, HSPA1A and/or HSPH1. Methods to measure nucleic acid expression are known in the art and may include PCR, quantitative PCR, RT-PCR, qRT-PCR, microarray or array.

In various embodiments, expression of HMOX1, HSPA1A and/or HSPH1 may be induced about 0.5-fold, about 1-fold, about 2-fold, about 3-fold, about 4-fold, about 5-fold, about 8-fold, about 10-fold, or more than 10-fold relative to a reference value. In various other embodiments, expression of HMOX1, HSPA1A and/or HSPH1 may be induced 0.5-fold, 1-fold, 2-fold, 3-fold, 4-fold, 5-fold, 8-fold, 10-fold, or more than 10-fold relative to a reference value. In other embodiments, expression of HMOX1, HSPA1A and/or HSPH1 may be induced about 10-fold, about 20-fold, about 30-fold, about 40-fold, about 50-fold, about 60-fold, about 70-fold, about 80-fold, about 90-fold, about 100-fold or more than 100-fold relative to a reference value. In still other embodiments, expression of HMOX1, HSPA1A and/or HSPH1 may be induced 10-fold, 20-fold, 30-fold, 40-fold, 50-fold, 60-fold, 70-fold, 80-fold, 90-fold, 100-fold or more than 100-fold relative to a reference value. In still yet other embodiments, expression of HMOX1, HSPA1A and/or HSPH1 may be induced about 100-fold, about 1000-fold, about 2000-fold, about 3000-fold, about 4000-fold, about 5000-fold, or more than 5000-fold relative to a reference value. In different embodiments, expression of HMOX1, HSPA1A and/or HSPH1 may be induced 100-fold, 1000-fold, 2000-fold, 3000-fold, 4000-fold, 5000-fold, or more than 5000-fold relative to a reference value. Any suitable reference value known in the art may be used. For example, a suitable reference value may be the expression of HMOX1, HSPA1A and/or HSPH1 in a sample that has not been contacted with a compound comprising Formulas (I), (Ia), (Ib), (Ic), or (Id). In another example, a suitable reference value may be the expression of HMOX1, HSPA1A and/or HSPH1 in a subject, or group of subjects, of the same species that has no clinically detectable symptom of cancer. In another example, a suitable reference value may be expression of HMOX1, HSPA1A and/or HSPH1 in a subject, or group of subjects, of the same species that has no clinically detectable cancer. In another example, a suitable reference value may be the background signal of the assay as determined by methods known in the art. In another example, a suitable reference value may be a measurement of the expression of HMOX1, HSPA1A and/or HSPH1 in a reference sample obtained from the same subject. The reference sample may be obtained from a subject when the subject had no clinically detectable symptom of cancer. A skilled artisan will appreciate that it is not always possible or desirable to obtain a reference sample from a subject when the subject is otherwise healthy. For example, when monitoring the effectiveness of a therapy or efficacy of dehydroleucodine or a compound comprising Formulas (I), (Ia), (Ib), (Ic), or (Id), a reference sample may be a sample obtained from a subject before therapy or administration of dehydroleucodine or the compound comprising Formulas (I), (Ia), (Ib), (Ic), or (Id) began. In an additional example, a suitable reference sample may be from an individual or group of individuals that has been shown not to have cancer.

(c) Optional Contact

In certain embodiments, the method may further comprise contacting the cell with at least one chemotherapeutic agent and/or a radiotherapeutic agent. The chemotherapeutic agent and/or radiotherapeutic agent may be administered concurrently or sequentially with dehydroleucodine or the compound comprising Formulas (I), (Ia), (Ib), (Ic), or (Id).

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1 BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent may be determined by a skilled practitioner.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein can exist in tautomeric, geometric or stereoisomeric forms. The present disclosure contemplates all such compounds, including cis- and trans-geometric isomers, E- and Z-geometric isomers, R- and S-enantiomers, diastereomers, d-isomers, l-isomers, the racemic mixtures thereof, and other mixtures thereof. Pharmaceutically acceptable salts of such tautomeric, geometric or stereoisomeric forms are also included within the invention. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. The terms "cis" and "trans" (or "E" and "Z"), as used herein, denote a form of geometric isomerism in which two carbon atoms connected by a double bond will each have a hydrogen atom on the same side of the double bond ("cis") or on opposite sides of the double bond ("trans").

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (0), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted (i.e. replaced) with a heteroatom such as nitrogen, oxygen, silicon, phosphorous, boron, or a halogen atom, and moieties in which the carbon chain comprises additional substituents. These moieties may include alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following examples illustrate various iterations of the invention.

Example 1. Synthesis of Dehydroleucodine Analogs

The sesquiterpene lactone dehydroleucodine (FIG. 2) was isolated from *Gynoxys verrucosa* Wedd by the following procedure: the air-dried parts of *Gynoxys verrucosa* (200 g) were extracted with ethyl acetate (EtOAc) (dynamic maceration for 5 h) at room temperature and concentrated under reduced pressure. The extract (14 g) was filtered through a reverse phase $C_{18}$ column (LiChroprep Merck 25-40 μm) with a mixture MeOH/$H_2O$ 85:15, for the removal of chlorophylls. The filtrate (7 g) was fractioned by column chromatography using a hexane-EtOAc gradient. Dehydroleucodine (DHL) was eluted in the hexane: EtOAc (85:15) fraction (0.7 g) and recrystallized from EtOAc as a white crystalline solid.

Figure 2:
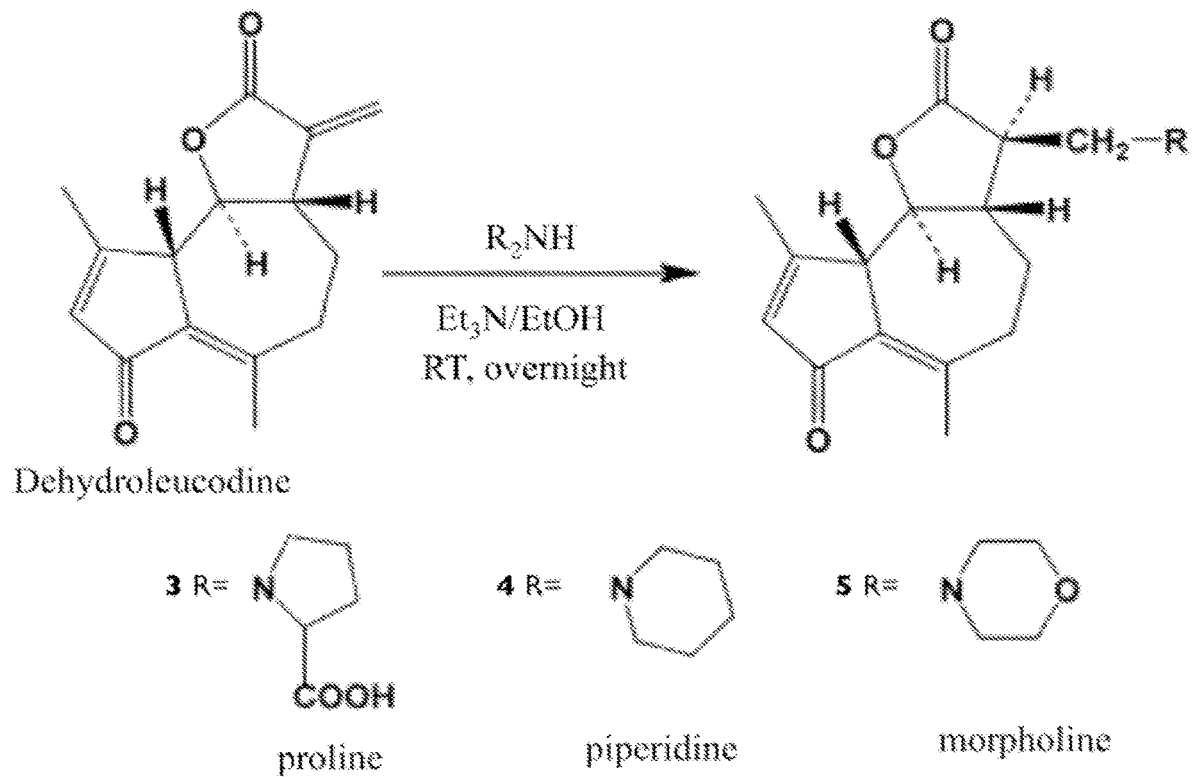
FIG. 2 depicts a schematic of the synthesis of dehydroleucodine adducts.

In an effort to develop more water-soluble compounds, dehydroleucodine derivatives were synthesized through a stereoselective conjugate addition of a primary or secondary amine to the α-methylene-γ-lactone moiety (FIG. 2). Thus, the exocyclic conjugated methylene in the lactone ring of DHL was reacted with the appropriate primary or secondary amine in a one-step reaction. The general synthetic procedure was the following: a solution of dehydroleucodine (0.22 mmol) in EtOH (6 mL) was treated with various primary or secondary amines (4.4 mmol) in the presence of triethylamine ($Et_3N$) and the mixture was stirred at room temperature overnight. The reaction mixture was evaporated under reduced pressure and the residue was further purified by silica gel flash chromatography to yield products 3-5. In all cases, a good yield (60-91%) of a single diastereomeric product was obtained. Compounds DHL-proline (3), DHL-piperidine (4) and DHL-morpholine (5) were used to provide a basis for SAR analysis.

Figure 3:
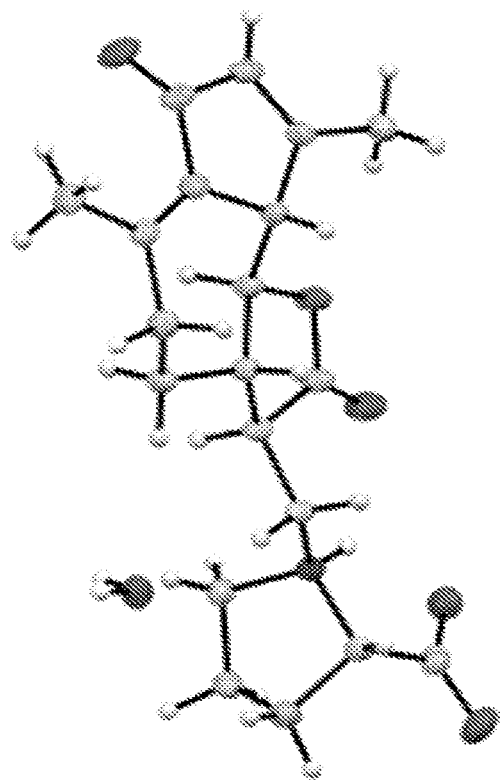
FIG. 3 depicts the 3-D-ORTEP projection of the X-ray crystal structure of DHL-proline with 50% probability ellipsoids.

DHL-proline (3) was obtained following the above general procedure in the presence of L-proline, and then purified by flash chromatography (silica gel, 0-50% hexane/ethyl acetate) (Yield: 44.3 mg (60%)). DHL-proline was obtained as a white powder; it has the molecular formula $C_{20}H_{25}NO_5$ based on the HRMS (m/z 360.1823 [M+H]$^+$) and NMR data. The IR (ATR) spectrum showed absorption bands ($V_{max}$) at 3510 (COO—H st), 1760 (C=O st γlactone) and 1670 (α-β unsaturated C=O), 1645, 1633, 1613 (C=C st) cm$^{-1}$. Complete $^1$H and $^{13}$C NMR data is provided in Table 1. The assignments of its $^1$H and $^{13}$C NMR resonances have been done involving two-dimensional experiments COSY, HMQC, ROESY and HMBC. The proton and carbon resonances appeared with almost the same chemical shifts and similar multiplicities as in DHL, except for the signals for H-12 at δ 2.25 and the signals corresponding to H-13 which appeared as a doublet at δ 1.27 in the $^1$H NMR spectrum, suggesting the presence of a secondary methyl group on the lactone ring. This was consistent with analogous changes in the $^{13}$C NMR spectrum. Thus, a large (anti) H-8/H-12$^3$J coupling, as well as a ROESY peak between H-12 and H-9, was observed, indicating that these hydrogens are in the same molecular face. In addition, a ROESY peak between H-12 and H-8 indicated that these hydrogens also lie on the same face. Finally, the structure of compound 3 was confirmed by X-ray crystallographic analysis, and a perspective ORTEP plot is shown in FIG. 3. The crystal structure of DHL-proline shows that the H atom has migrated to the N atom of this molecule. The difference electron density map clearly shows this H atom, and shows nothing at the COO group. Also, the H atoms of the included water molecule were found by difference map.

TABLE 1

NMR Spectroscopy Data (500 MHz) of DHL-Proline

| Position | $δ_H$ | $δ_C$ | HMBC | COSY |
|---|---|---|---|---|
| 1 | | 170.3 | | |
| 2 | 6.17 | 135.8 | 196.4, 170.3, 131.8, 52.4, 19.9 | 3.58, 2.28 |
| 3 | | 196.4 | | |
| 4 | | 131.7 | | |
| 5 | | 153.0 | | |
| 6 | 2.46 | 37.4 | 153.0, 131.7, 52.9, 25.6, 21.7 | 2.33 |
|   | 2.33 | | | |
| 7 | 2.08 | 25.6 | 153.0, 84.6, 52.4, 37.4 | 2.46, 2.33, 1.44, |
|   | 1.44 | | 153.0, 84.6, 52.4, 37.4 | 24.6, 2.33, 2.08 |
| 8 | 2.34 | 52.4 | 153.0, 131.7, 52.9, 25.6, 21.7 | |
| 9 | 3.75 | 84.6 | 173.0, 131.7, 52.4, 43.4, 29.2, 25.6, 24.2 | 3.50, 2.34 |
| 10 | 3.50 | 52.4 | 170.3, 131.7, 135.8, 84.6, 52.4 | 6.17, 3.75, [2.42]$^a$, [2.25] |
| 11 | | 176.0 | | |
| 12 | 2.76 | 43.4 | 176.0 | 3.41, 3.21, 2.34 |
| 13 | 3.41 | 52.8 | 176.0, 69.2, 54.7, 43.4 | 3.21, 2.76 |
|    | 3.21 | | 176.0, 54.7, 52.4, 43.4 | 3.41, 2.76 |

TABLE 1-continued

NMR Spectroscopy Data (500 MHz) of DHL-Proline

| Position | $\delta_H$ | $\delta_C$ | HMBC | COSY |
|---|---|---|---|---|
| 14 | 2.28 | 19.9 | 170.3, 135.8, 52.4 | 6.17, 3.50 |
| 15 | 2.42 | 21.7 | 153.0, 131.7, 37.4 | 3.50 |
| 16 | 3.66 | 54.7 | 69.2, 52.8, 29.4, 24.2 | 2.80, 2.0 |
|  | 2.80 |  | 52.8, 29.4, 24.2 | 3.66, 2.0 |
| 17 | 2.00 (2H) | 24.2 | 69.2, 54.7, 29.4 | 3.66, 2.8 |
| 18 | 2.32 | 24.4 | 153.0, 131.7, 52.9, |  |
|  | 2.23 |  | 25.6, 21.7 |  |
| 19 | 3.73 | 69.2 | 2.32, 2.23 |  |
| 20 |  | 173.0 |  |  |

*a* Numbers in square brackets denote weak long range correlations

DHL-piperidine (4) was obtained following the above general procedure in the presence of piperidine, and then purified by flash chromatography (silica gel, 0-80% hexane/ ethyl acetate) (Yield: 29.40 mg (66%)). DHL-piperidine was isolated as a pale yellow solid with the molecular formula $C_{20}H_{27}NO_3$ based on the HSMR (m/z 330.2075 [M+H]$^+$). Its UV spectrum in (MeOH) shows two peaks at λ (log ε) 204 (3.66) nm and 256 (4.14) nm. The IR (ATR) spectrum shows bands at 2936 (C—H st), 1773 (C=O st γlactone), 1683 (α-β unsaturated C=O), 1617, 1637 (C=C st) cm$^{-1}$. The EI spectrum shows one main fragment at m/z 244 (100) [dehydroleucodine]. The $^1$H and $^{13}$C NMR chemical shifts are shown in Table 2. Assignments of all proton and carbon resonances were achieved involving the 2D NMR techniques COSY, ROESY and HMBC.

TABLE 2

NMR Spectroscopy Data (500 MHz) of DHL-piperidine

| Position | $\delta_H$ | $\delta_C$ | HMBC | COSY |
|---|---|---|---|---|
| 1 |  | 170.1 |  |  |
| 2 | 6.16 | 135.6 | 196.1, 170.1, 132.0, 52.8, 20.0 | 3.43, 2.29, 6.16 |
| 3 |  | 196.1 |  |  |
| 4 |  | 132.0 |  |  |
| 5 |  | 152.8 |  |  |
| 6 | 2.43 | 37.9 | 152.8, 132, 26.5, 54.8, 37.9 | 2.20, 2.40, 2.43 |
|  | 2.30 |  |  |  |
| 7 | 2.40 | 26.5 |  | 2.60 |
|  | 1.34 |  |  |  |
| 8 | 2.20 | 54.8 | 84.3, 52.8 | 2.40, 2.41, 3.60, 3.43, 2.79 |
| 9 | 3.60 | 84.3 | 170.2, 132.0, 52.8, 20.0 | 6.16, 3.60, 3.43, 2.20, 2.29 |
| 10 | 3.42 | 52.8 | 196.1, 170.1, 152.8, 135.7, 132.0, 84.3, 54.8 | 3.60, 6.16, 3.43, 2.29, 2.41 |
| 11 |  | 176.9 |  |  |
| 12 | 2.41 | 44.0 |  | 2.20, 2.60, 2.79 |
| 13 | 2.79 | 58.2 | 176.9, 54.8, 44.0, 176.9, 54.8, 44.0 | 2.41, 2.20, 2.79, 2.40, 2.20 |
|  | 2.60 |  |  |  |
| 14 | 2.29 | 20.0 | 170.2, 152.6, 135.6, 131.9, 52.8, 26.2 | 6.16, 3.43 |
| 15 | 2.43 | 21.7 |  | 3.4 |
| 16 |  |  |  | 2.32, 2.60, 2.79, 2.42, 2.60, 2.79 |
| 17 | 1.54 | 26.2 | 55.0, 26.2, 24.3 | 2.42, 1.43 |
| 18 | 1.43 | 24.3 | 55.0, 26.2 | 1.54, 2.42 |
| 19 |  |  | 55.0, 26.2, 24.3 |  |
| 20 | 2.42 | 55.0 |  | 2.32, 2.60, 2.79, 2.42, 2.60, 2.79 |
|  | 2.32 |  |  |  |

Figure 4:
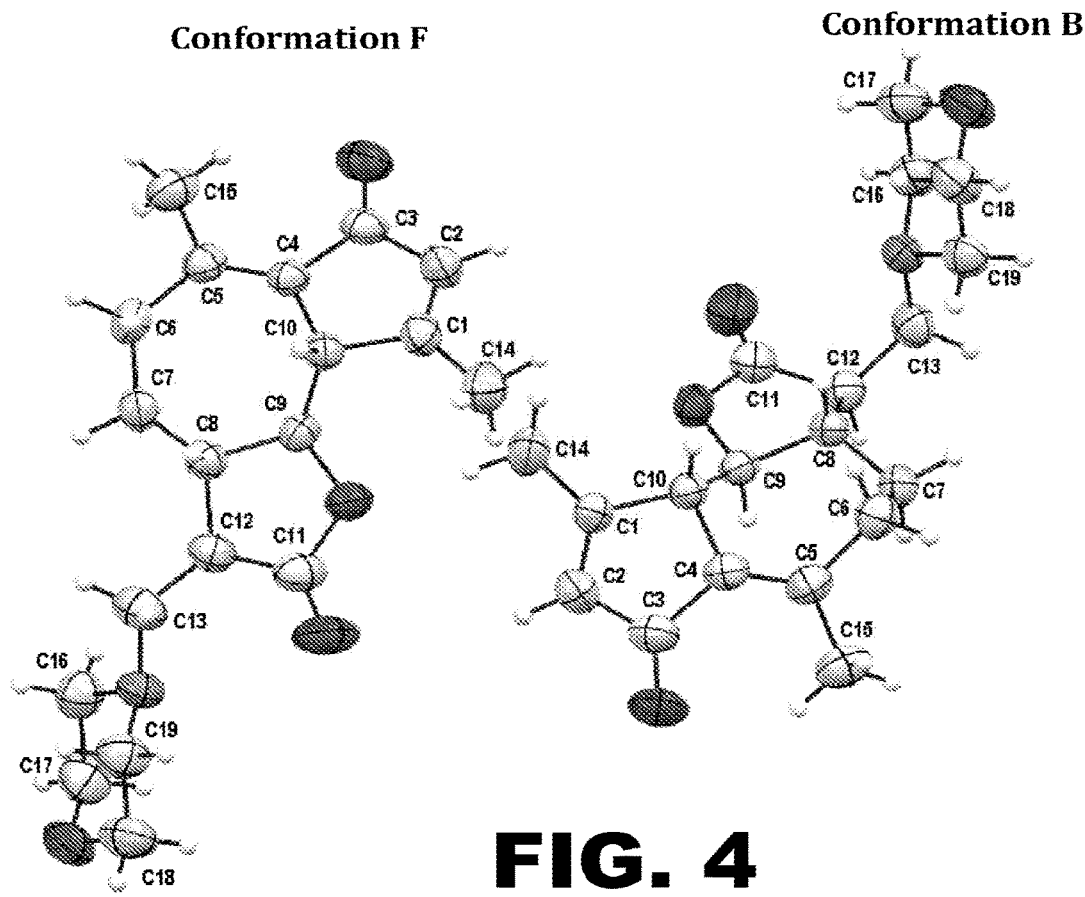
FIG. 4 depicts the 3-D-ORTEP projection of the X-ray crystal structure of DHL-morpholine with 50% probability ellipsoids.
Figure 5:
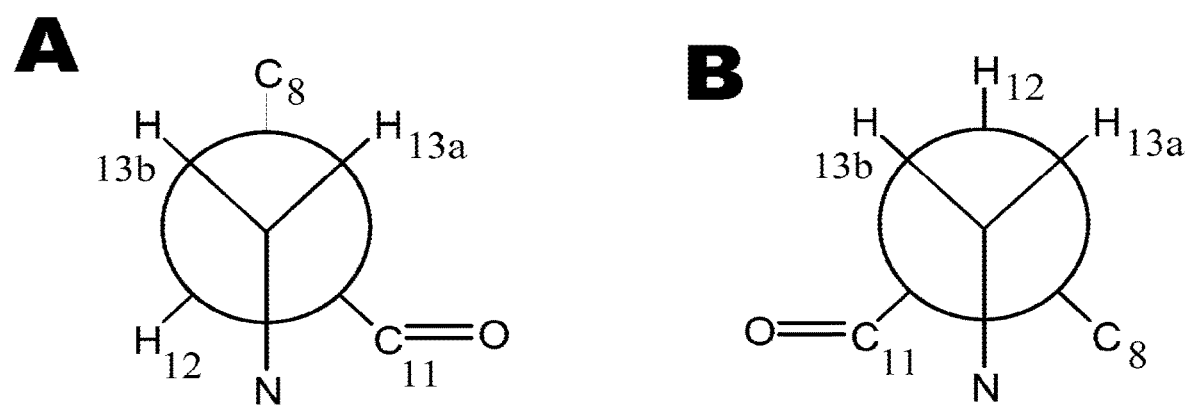
FIG. 5A and FIG. 5B depict the conformations of DHL-morpholine. The crystal unit cell is composed for two distinct molecular structures of DHL-morpholine. One conformation is (FIG. 5A) trans for C-13-N and C—H-12 bonds while the other is (FIG. 5B) gauche cis.

DHL-morpholine (5) was obtained following the above general procedure in the presence of morpholine, and then purified by flash chromatography (silica gel, 0-80% hexane/ ethyl acetate) (Yield: 61.80 mg (91%)). DHL-morpholine was obtained as colorless crystals with mp 158-159° C. with the molecular formula assigned as $C_{19}H_{25}NO_4$ on the basis of its HRMS data (m/z 332.1848 [M+H]$^+$). Its UV spectrum (MeOH) shows two peaks at λ (log ε) 204 (3.99) nm and 256 (4.28) nm. The IR (ATR) spectrum shows bands at 2930 (C—H st), 1770 (C=O st γlactone), 1680 (α-β unsaturated C=O), 1640, 1610 (C=C st) and 1110 (C—O—C) cm$^{-1}$. The EI spectrum showed the molecular ion at (m/z 331.10) with low intensity (2), with other fragments at m/z (rel. int.) 300 (6) [M$^+$—CH$_3$O], 288 (3) [M$^+$—C], 244 (0.5) [$C_{15}O_3H_{16}^+$], 100.1 (100) [$C_4O_2H_5N^+$], 86 (9) [$C_3O_2H_3N^+$], 71.1 (1) [$C_4NH_8^+$] and 57.1[$CNH_4^+$] (2). The $^1$H and $^{13}$C NMR assignments are given in Table 3. For all protons and carbon resonances were achieved by COSY, ROESY, HSQC and HMBC experiments. The relative configuration of compound 5 was determined by analysis of its NOESY data. An NOE correlation was observed between H-8 and H-13 methylene protons but not H-12. H-8 shows three large (10-12 Hz) vicinal couplings to H-9, H-12 and one of the H-7 (at delta 1.36) protons, indicating that it is anti to H-9, H-12 and delta 1.36 proton. H-9 shows strong NOE peaks to both H-12 and the delta 1.36 proton. Thus H-8 and H-12 are on opposite faces of the molecule. On the basis of this evidence, the absolute stereochemistry of compound 5 was determined. Ultimately, the structure of 5 was confirmed by X-ray crystallographic analysis, and a perspective ORTEP plot is shown in FIG. 4. The crystal unit cell is composed for two distinct molecular structures of DHL-morpholine, as shown in FIG. 5; one conformation is trans for C-13-N and C—H-12 bonds while the other is gauche cis. These conformations are represented in FIG. 5.

TABLE 3

NMR Spectroscopic Data (500 MHz) of DHL-morpholine

| Position | $\delta_H$ | $\delta_C$ | HMBC | COSY |
|---|---|---|---|---|
| 1 | | 169.9 | | |
| 2 | 6.17 (q, 1.3) | 135.5 | 196.0, 169.9, 131.9, 52.4, 19.7 | 3.43[2.29][a] |
| 3 | | 196.0 | | |
| 4 | | 131.9 | | |
| 5 | | 152.4 | | |
| 6 | 2.43 (m) | 37.4 | | |
|   | 2.30 (m) | | | |
| 7 | 2.34 (m) | 26.1 | 152.4, 84.0, 54.1, 37.4 | 2.43, 2.34, 2.30, |
|   | 1.36 (m) | | | 2.24 |
| 8 | 2.24 (m, −12, 12, 10, 3) | 54.1 | | 3.62, 2.41, 2.34, 1.36 |
| 9 | 3.62 (t, 10.1) | 84.0 | 131.9, 43.7, 26.1, | 3.43, 2.24 |
| 10 | 3.43 (bd, 10) | 52.4 | 196.0, 169.9, 152.4, 135.5, | 6.17, 3.62, [2.43][a], |
|   | | | 131.7, 84.0, 54.1 | [2.29] |
| 11 | | 176.3 | | |
| 12 | 2.41 (m) | 43.7 | | |
| 13 | 2.84 (dd, 13.2, 4.7) | 57.2 | 176.3, 54.1, 43.7, 176.3, 54.1, | 2.63, 2.41, 2.84, |
|   | 2.63 (dd, 13.2, 7.4) | | 43.7 | 2.41 |
| 14 | 2.29 (3H, dd, 1.3, 0.9) | 19.7 | 169.9, 135.5, 52.4 | [6.17], [3.43] |
| 15 | 2.43 (3H, bs) | 21.3 | 152.4, 131.9, 37.4 | [3.43] |
| 16 | 2.51 (2H, m) | 53.9 | 66.7, 53.9 | 2.43 |
|   | 2.43 (2H, m) | | | 2.51 |
| 17 | 3.69 (4H, m) | 66.7 | 66.7, 53.9 | 2.51, 2.43 |
| 18 | 3.69 (4H, m) | 66.7 | 66.7, 53.9 | 2.51, 2.43 |
| 19 | 2.51 (2H, m) | 53.9 | 66.7, 53.9 | 2.43 |
|   | 2.43 (2H, m) | | | 2.51 |
| 20 | | 169.9 | | |

[a]Numbers in square brackets denotes weak long range correlations.

DHL-tyramine: The compound was obtained by following the above general procedure in the presence of tyramine, and a mixture of EtOAc/Hexane 10% used as eluent in flash chromatography medium pressure.

Example 2: Conformations of DL-Morpholine

In order to determine which of the two morpholine conformations is present in solution, both conformers observed in the X-ray crystal structure were analyzed. Thus, the vicinal hydrogens, one at C-12 and two at C-13 were considered for the measurements of dihedral angles. The single crystal unit is composed of two molecules, each bearing the C-13/N bond of the morpholine moiety in opposite directions while preserving its chair conformation. The H-12/H-13 hydrogen-hydrogen dihedral angles for each molecule that composes the crystal unit were measured using Mercury software, and these values were used to estimate the coupling constants using a generalized Karplus curve of vicinal couplings for protons; values are given in Table 4.

According to the couplings observed experimentally, the $^2J$ coupling of C-13 hydrogens is 13.2 Hz with further splittings of 7.4 and 4.7 Hz with H-12. This implies that the dominant average conformation is where H-12 has one near anti plus a gauche relationship with the hydrogens at C-13, while the population having an almost equal gauche relationship of H-12 to both C-13 hydrogens is negligible.

TABLE 4

Hydrogen-Hydrogen dihedral angles for Conformations 1 and 2

| | Dihedral angle Angle (J)[a] | |
|---|---|---|
| Fragment | Conformation 1 | Conformation 2 |
| H-12-C-12-C-13-H-13$_a$ | 162.53° (11 Hz) | 61° (4 Hz) |
| H-12-C-12-C-13-H-13$_b$ | 79.91° (2.5 Hz) | −56° (4.5 Hz) |

[a]Estimated using Karplus curve

The atoms in a molecule can adopt many different positions (conformations) without undergoing a rearrangement of their chemical bonds. Transformations from one configuration to another occur via rotation about a single bond with minor alterations of bond angle and length. In order to find the lowest-energy conformations of a molecule there are a number of methods available in SYBYL 8.1. Grid-Search analysis was used, which systematically searches a molecule with minimization of every conformation. The conformers were obtained by performing systematic torsion angle changes around the C12 and C13 single bond with 10-degree increments, using the Steepest Descendent method for the energy minimization with 1000 iterations and a gradient of 0.05. Starting geometries were optimized using MOPAC electrostatic charges and TRIPOS force field, with dielectric function distance and 8.0 as NB cutoff.

Figure 6:
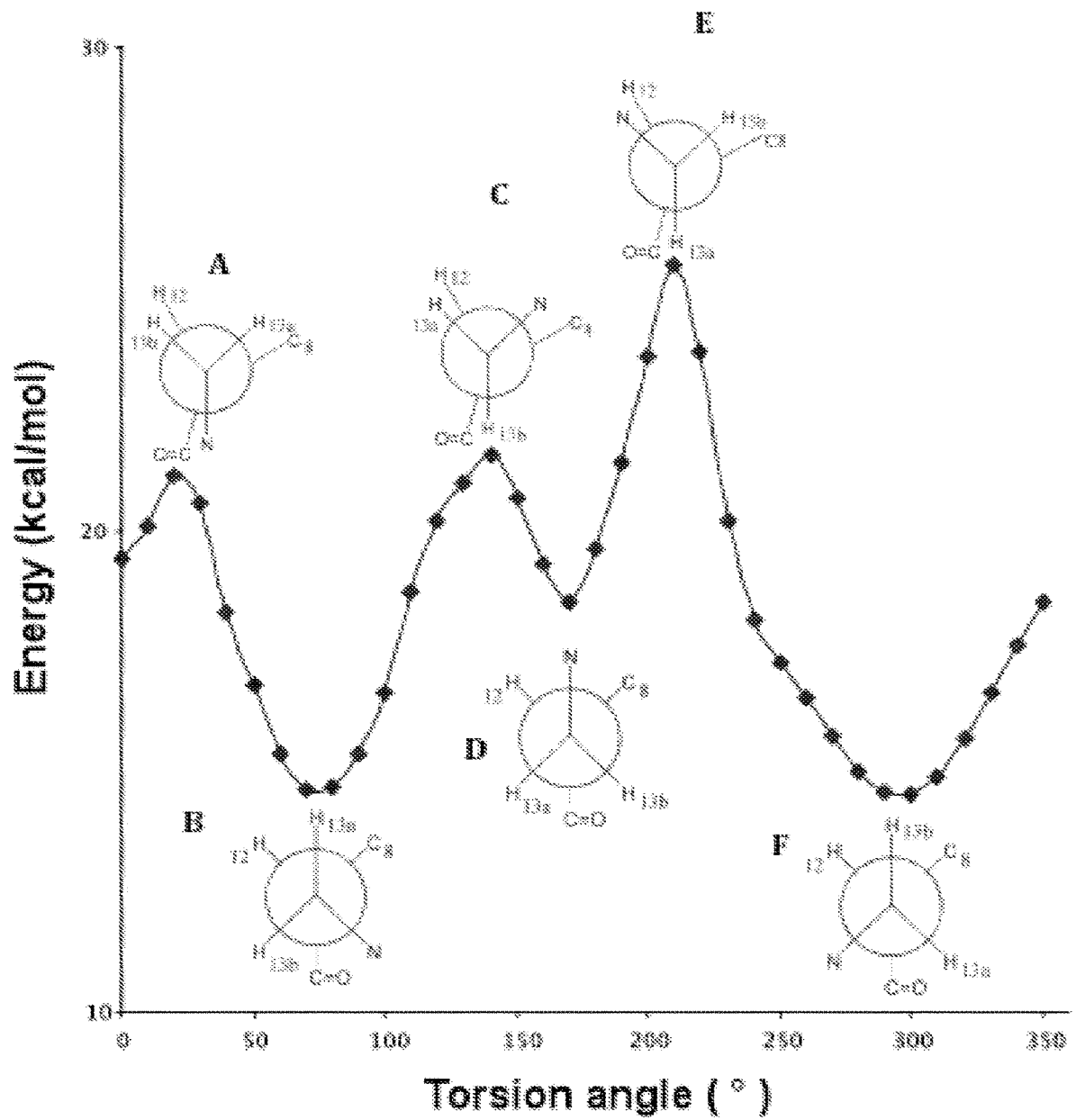
FIG. 6 depicts the conformational analysis of DHL-morpholine. The results of Grid-Search conformation analysis showed three minimums (B, D, F) and three maximums (A, C, E). The minimums corresponded with the staggered conformations. Two of the minimums, B and F, with energies of 14.60 and 14.61, respectively, correspond with the conformations displayed in the crystal structure unit cell. The three maximums, A, C and E, with energies of 21.00, 21.50 and 25.40, respectively, correspond to the eclipsed conformations.

The results of the Grid-Search conformation analysis showed three minimums and three maximum (FIG. 6). These minimums correspond with the staggered conformations. Two of these three minimums, conformations B and F, with energies of 14.60 and 14.61 respectively, correspond with the conformations displayed in the crystal structure unit cell. The difference in energy between these conformations is very small: about 0.01 kcal/mol. The three maximums, conformations A, C and E with energies of 21.00, 21.50 and 25.40 kcal/mol respectively, correspond to the eclipsed conformations.

Example 3: Cytotoxic Activity of DHL and its Derivatives on Cancer Cells

In order to assess the structure-activity relationship of DHL and its derivatives, DHL and its derivatives were evaluated against eight human leukemia cell lines. Cell lines were cultured in Iscove's Modified Dulbecco's Medium (IMDM) supplemented with 10%~20% fetal bovine serum (FBS) according to culture conditions indicated by ATCC and 1% penicillin/streptomycin (Pen/Strep) at 37° C. and 5% $CO_2$. The cells were seeded into 96-well plates and kept at a concentration of 0.5 million cells per mL. The samples were treated with DHL, Leucodine, DHL-Morpholine, DHL-Proline, DHL-Piperidine, and PTL at varying concentrations in triplicates. Cell viability was determined after incubating for 48 hours. The cells were stained with annexin V-fluorescein isothiocyanate or phycoeritrine (FITC/PE) and 7-aminoactinomycin (7-AAD) to detect phosphatidylserine exposition and cell permeability, respectively. At least 50,000 events were recorded per condition on either an LSR-II or LSR-Fortessa flow cytometer (BD Biosciences). Data analysis was conducted using FlowJo 9.6 software for Mac OS X (TreeStar). Cells that were negative for annexin V and 7-AAD were scored as viable.

The results are shown in Table 5, with the inclusion of the extract G. Verrucosa as a reference. This is one of the first studies where DHL, another plant-derived SL, has been examined in AML. As seen from Table 5, DHL has potent activity against multiple AML leukemic cell lines after 48 hours of treatment, with $LD_{50}$ values ranging from 5.02-18.95 μM in the various leukemic cell lines tested. Each cell line was also tested with PTL at 10 μM for comparison, with an average viability of 70.4% after 48 hours. Thus, DHL displayed more potent anti-leukemic activity than PTL in most samples. Leucodine was not found to be active, suggesting that the exocyclic methylene in DHL is necessary for the observed activity. The in vitro cytotoxicity of the amino derivatives of DHL is maintained, but at a more moderate level, with DHL-Proline serving as the most potent derivative.

Example 4: Cytotoxic Activity of DHL and its Derivatives on Normal Cells

When determining the potential of a new chemotherapeutic agent for use in patients, it is important that the drug effectively targets tumor cells without causing significant harm to noncancerous cells. In order to better establish our understanding of DHL as an anticancer drug, we tested the activity of DHL and its derivatives on normal bone marrow (n=1) and peripheral blood (n=3) mononuclear cells. Bone marrow and peripheral blood samples were obtained from volunteer donors. Mononuclear cells were isolated from the samples using Ficoll-Plaque density gradient separation. Cells were cultured in serum-free medium (SFM) supplemented with cytokines (50 ng/ml rhFLT-3 ligand, 50 ng/ml rhSCF, 20 ng/ml rhIL-3, 20 ng/ml rhIL-6) for 1 h before the addition of drugs. The cells were seeded into 96-well plates and kept at a concentration of 0.5 million cells per mL. The samples were treated with DHL, Leucodine, DHL-Morpholine, DHL-Proline, DHL-Piperidine, and PTL at varying concentrations in triplicates. Cell viability was determined after incubating for 48 hours. The cells were stained with annexin V-fluorescein isothiocyanate or phycoeritrine (FITC/PE) and 7-aminoactinomycin (7-AAD) to detect phosphatidylserine exposition and cell permeability, respectively. At least 50,000 events were recorded per condition on either an LSR-II or LSR-Fortessa flow cytometer (BD Biosciences). Data analysis was conducted using FlowJo 9.6 software for Mac OS X (TreeStar). Cells that were negative for annexin V and 7-AAD were scored as viable.

Figure 7:
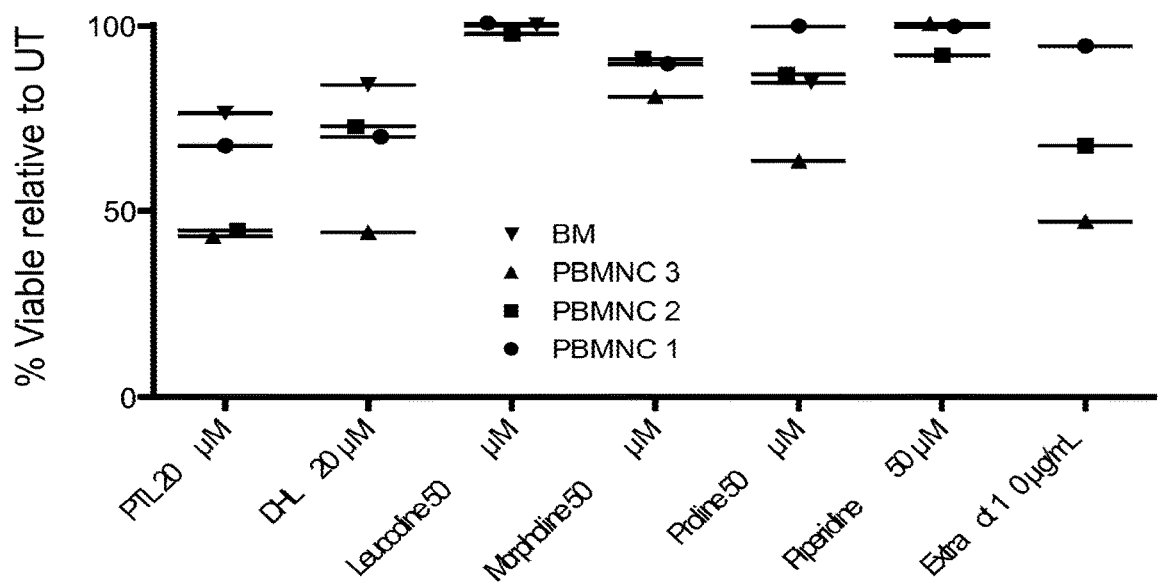
FIG. 7A and FIG. 7B depict graphs showing that DHL is significantly less potent in normal peripheral blood mononuclear cells (PBMNCs) than leukemic cells.
Figure 7:
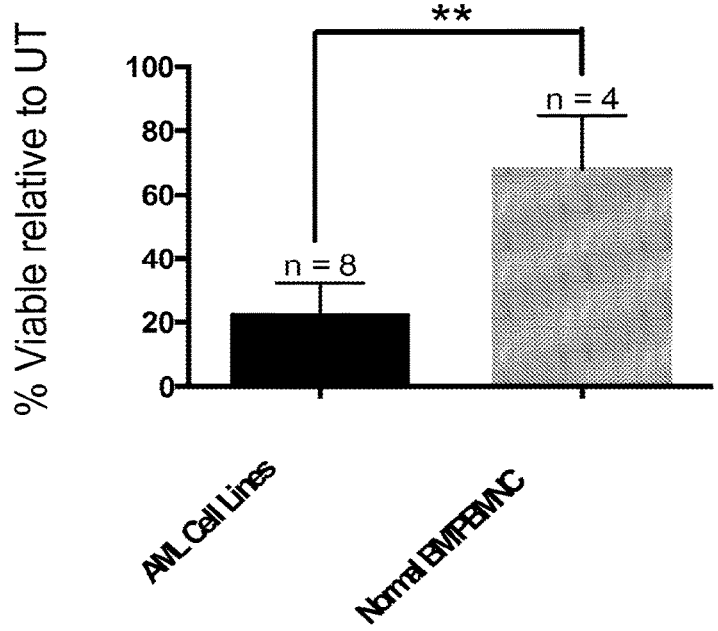

FIG. 7A displays the viability of the normal samples after 48 hours of treatment with either 20 μM DHL or 50 μM of the amino derivatives, with the inclusion of PTL and G. verrucosa extract to serve as references. Since these SL's are derived from plants, we initially expected there to be little toxicity. Leucodine and the amino derivatives display very little toxicity overall. DHL, however, was shown to have a similar cytotoxic effect as PTL. When compared to PTL, DHL was slightly less toxic to normal cells but more toxic in most of the AML cell lines. Importantly, FIG. 7B shows that DHL is significantly more potent to the AML cell lines tested (n=8) than to normal mononuclear cells (n=4, p=0.004). Thus, DHL has the cytotoxic profile to serve as a suitable chemotherapeutic agent.

Example 5: Mechanism of Action of DHL and its Derivatives

To better understand the mechanism by which DHL kills AML, the intracellular effects upon DHL treatment were

TABLE 5

Cytotoxic effects of DHL, its derivatives, and G. Verrucosa extract, expressed as $LD_{50}$ values (μM for DHL and derivatives of DHL, μg/mL for extract)

|  | DHL (μM) | Leucodine (μM) | DHL-Proline (μM) | DHL-Piperidine (μM) | DHL-Morpholine (μM) | G. Verrucosa Extract (μg/mL) |
|---|---|---|---|---|---|---|
| HL-60 | 14.13 | >160 | 50.2 | 96.5 | 166 | 4.254 |
| Kasumi-1 | 12.92 | >160 | 28.1 | >160 | >160 | 3.546 |
| KG-1 | 18.66 | >160 | 97.7 | 182 | 129 | 7.102 |
| MOLM-13 | 12.59 | >160 | 20.6 | 52.3 | >160 | 3.146 |
| MV4-11 | 5.02 | >160 | 23.3 | 66.9 | 21.1 | 2.98 |
| THP-1 | 16.82 | 121 | 26.7 | 59.3 | 54.4 | 6.957 |
| TUR | 12.18 | 105 | 35.9 | >160 | >160 | 5.715 |
| U-937 | 18.95 | >160 | 33.0 | >160 | 74.7 | 6.012 |

Figure 8:
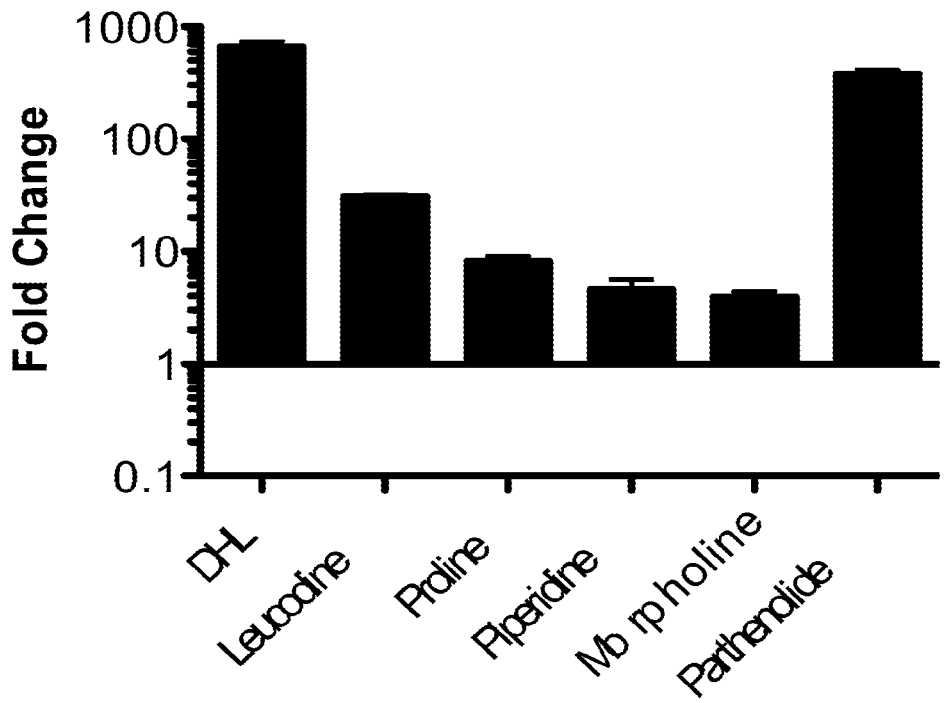
FIG. 8A, FIG. 8B, FIG. 8C and FIG. 8D depict graphs and a western blot showing that DHL and its derivatives induce HMOX-1 and HSPA1A, while downregulating NF-κB in MOLM-13 cells.
Figure 8:
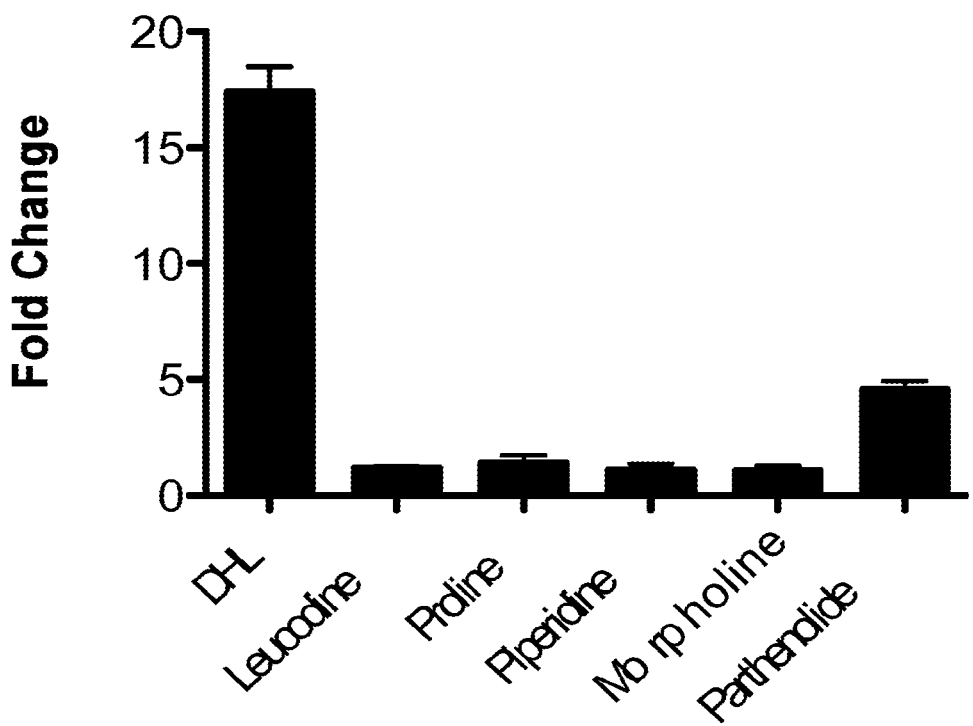
Figure 8:
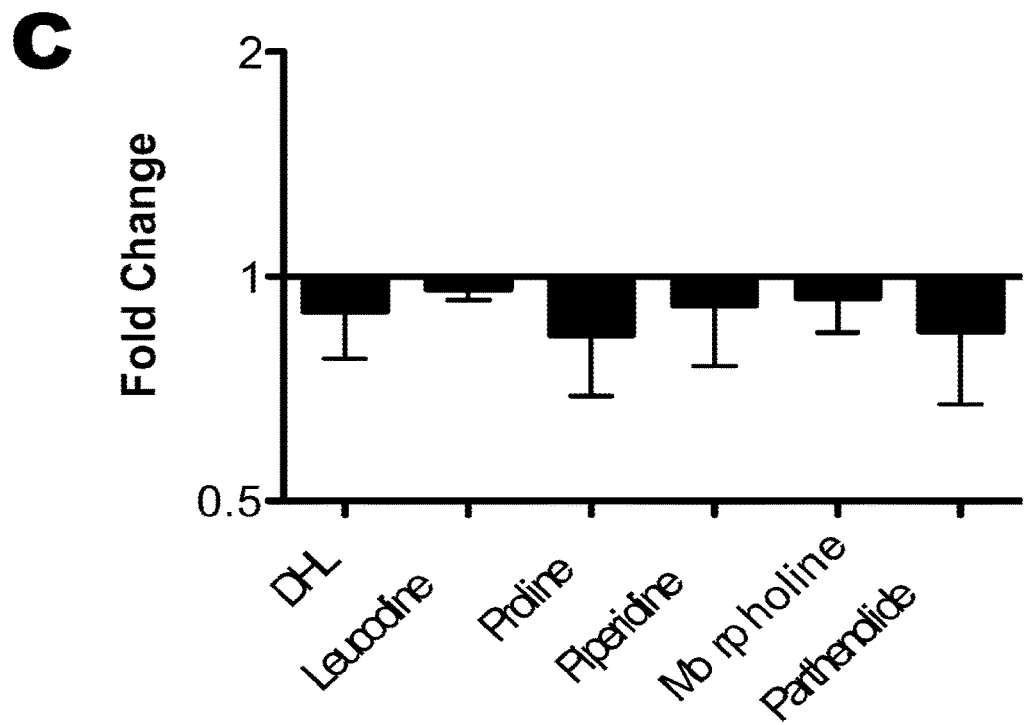
Figure 8:
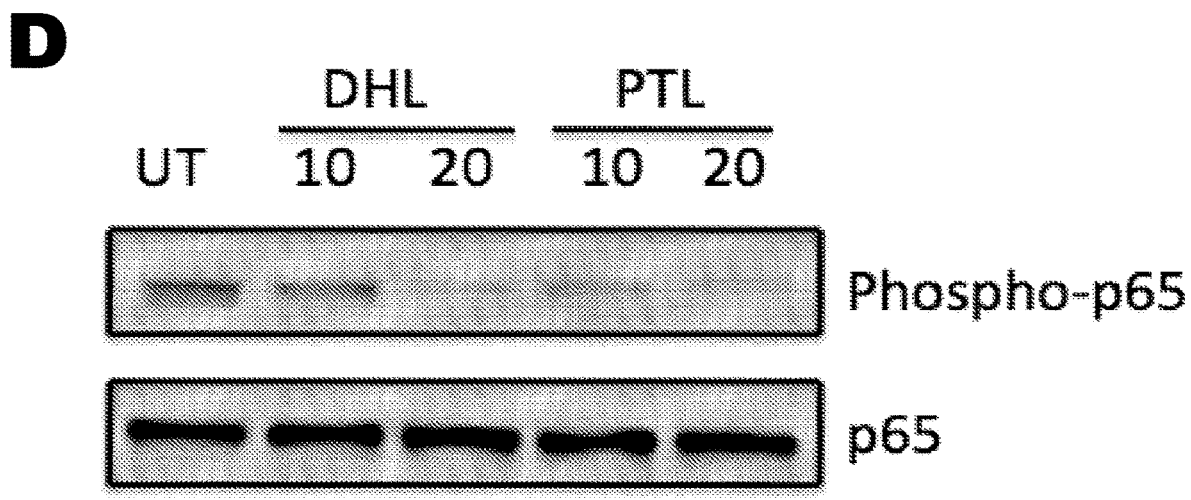
Figure 9:
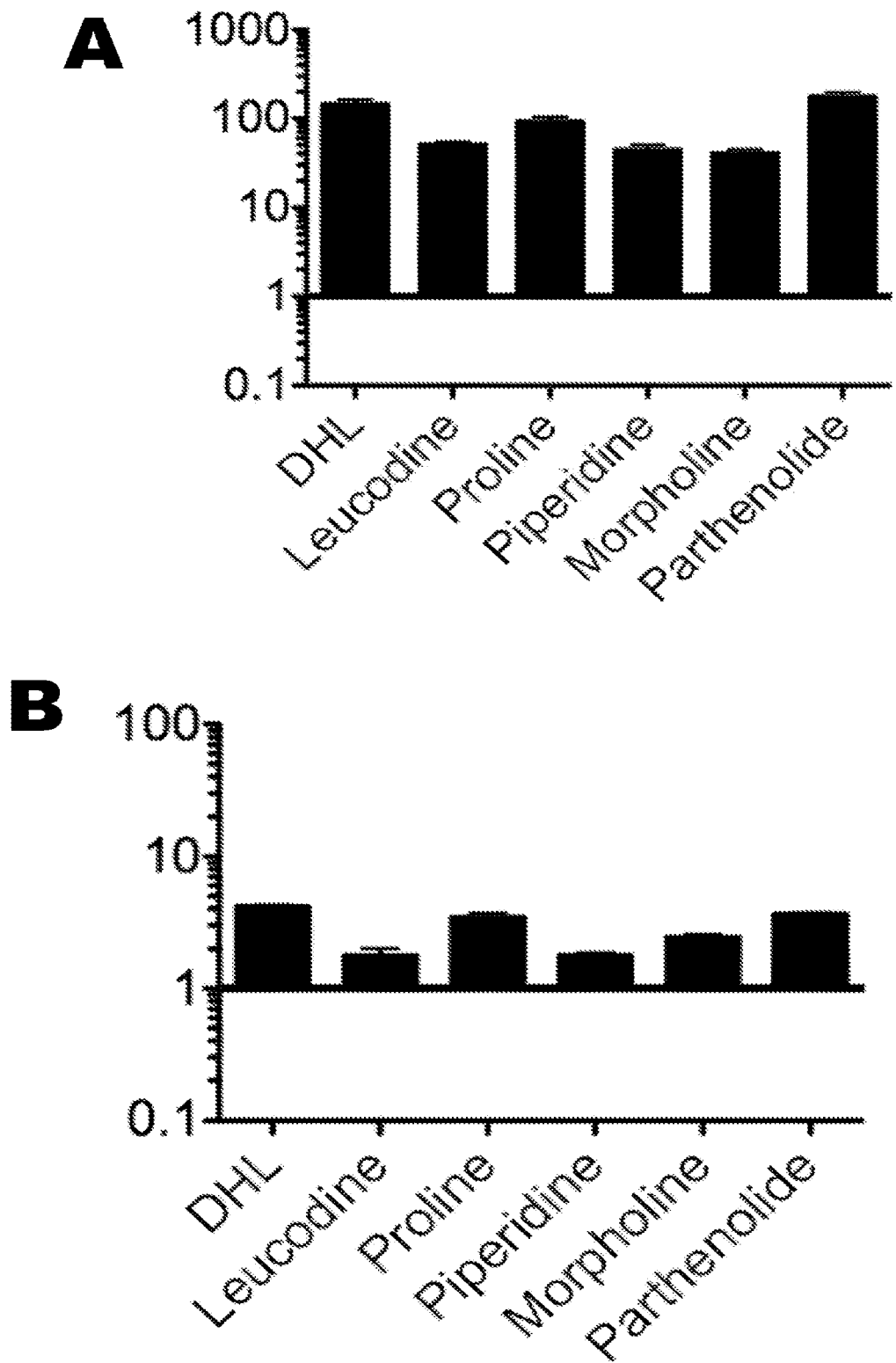
FIG. 9A and FIG. 9B depict graphs showing that DHL and its derivatives induce HMOX-1 and HSPA1A in MV-411 cells.

Drug range tested: [1.25-160 μM]

evaluated. To compare these intracellular effects of DHL and its derivatives, quantitative PCR was performed (FIG. 8 and FIG. 9). MOLM-13 or MV-411 cells were seeded at 0.5 million cells per milliliter. Cells were treated for 6 hours with 20 μM of DHL, Leucodine, DHL-Morpholine, DHL-Proline, DHL-Piperidine or PTL, and then collected. Total RNA was extracted using the Qiashredder and Qiagen Rneasy Mini kits. The real-time PCR was performed using the Taqman RNA to CT 1-Step kit. The thermal cycling conditions were one RT step (48° C., 15 minutes), Enzyme activation (95° C., 10 minutes) and 40 cycles of Denature (95° C., 15 seconds) and Anneal/extend (60° C., 1 minute). Quantitative PCR was performed using probes for HMOX-1 (Hs01110251_m1), HSPA1A (Hs00359163_s1), and NFKB1 (Hs00765730_m1). GADPH (Hs02758991_g1) was used as housekeeping gene, an internal control to normalize the variability in expression levels. Single-plex real-time PCR was performed in triplicates in a StepOne plus RealTime PCR system and analyzed with the StepOne Software. Fold change was calculated using the 2-DDCT method described by Livak and Schmittgen.

HMOX1 (Heme oxygenase 1) was measured to compare the relative levels of oxidative stress upon drug treatment (FIG. 8A and FIG. 9A). HSPA1A, the main stress-inducible isoform of HSP70, was also measured to compare oxidative stress (FIG. 8B and FIG. 9B). Although both DHL and PTL upregulated HMOX1 and HSPA1A, the higher fold changes by DHL treatment suggest that DHL may induce a greater amount of oxidative stress than PTL. Leucodine and the other DHL amino derivatives upregulated HMOX1 and HSPA1A in both MOLM-13 cells and MV-411 cells, although to a lesser extent in MOLM-13 cells. Interestingly, DHL-proline, when compared to the other DHL amino derivatives, upregulated HMOX1 and HSPA1A the most and also displayed the greatest cytotoxic effect on the AML cell lines, as seen from Table 5.

Figure 10:
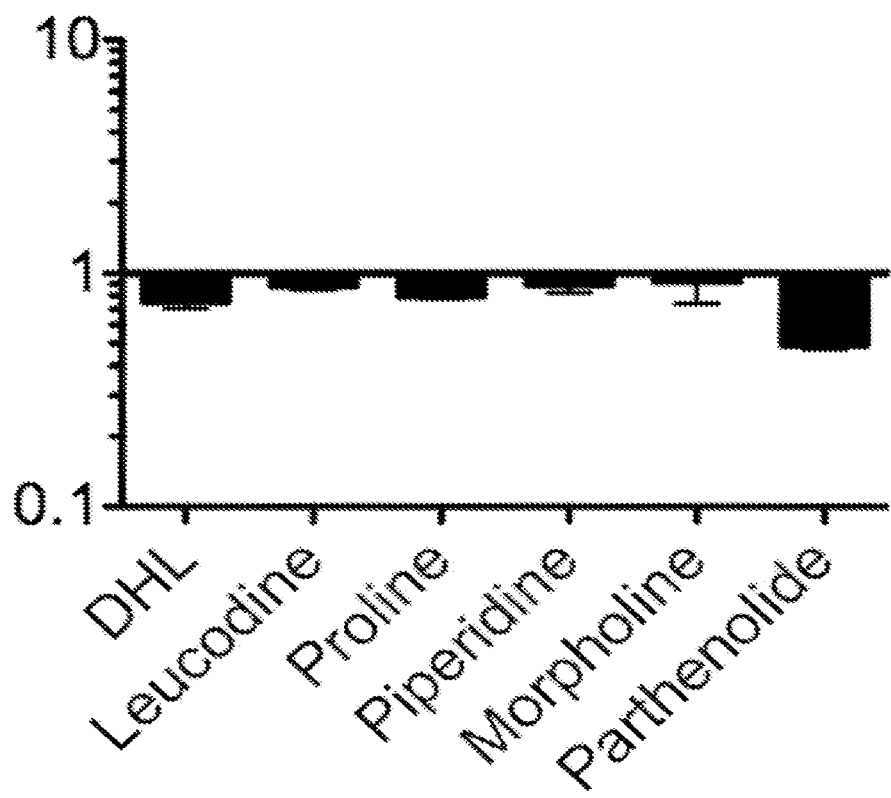
FIG. 10 depicts graphs showing that DHL and its downregulate NF-κB in MV-411 cells. Graphical representation of the fold changes of NF-κB in MV-411 cells, with the same experimental setup and analysis as FIG. 7A.
Figure 11:
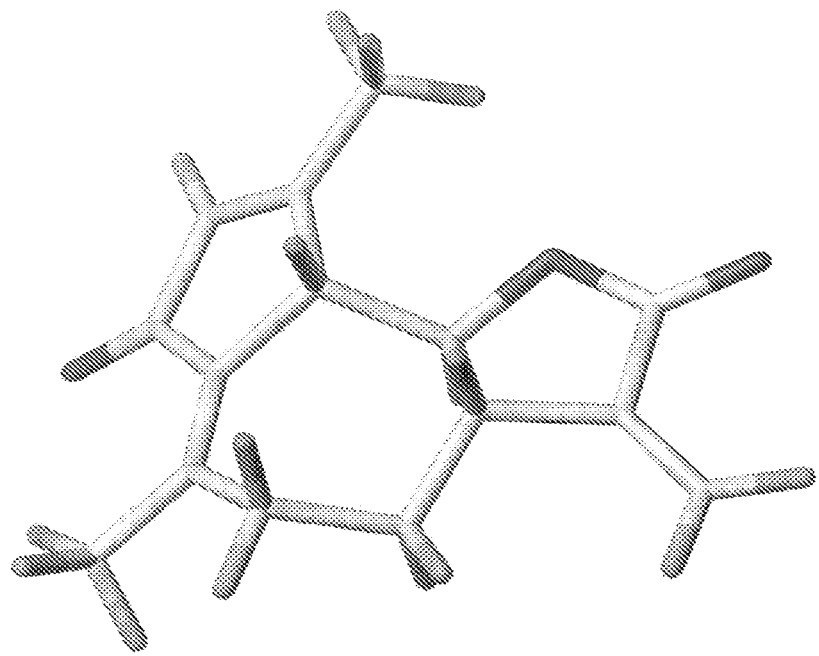
FIG. 11A and FIG. 11B depict the structures of DHL and parthenolide, respectively. DHL is structurally more rigid than parthenolide.
Figure 11:
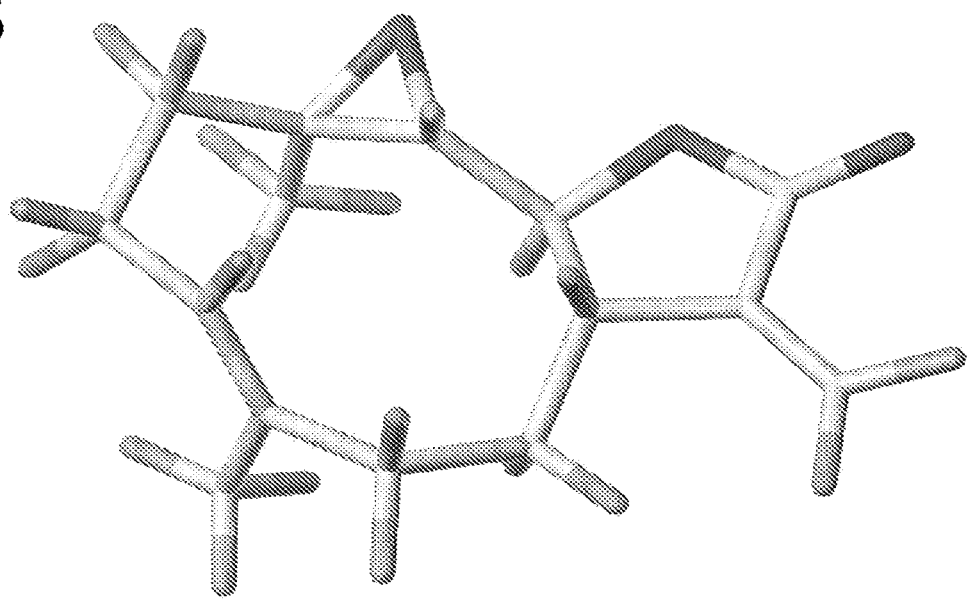

PTL is a SL that has been shown to induce apoptosis on leukemic stem and progenitor cells through inhibition of NF-κB.[4] As a comparison, NF-κB transcript levels were measured upon drug treatment in MOLM-13 cells (FIG. 8C) and MV-411 cells (FIG. 10). DHL, leucodine, and the DHL amino derivatives slightly downregulated NF-κB, while PTL treatment displayed the highest degree of downregulation.

In addition, the levels of phospho-p65 and total p65 by Western blot upon drug treatment of MOLM-13 cells was evaluated (FIG. 8D). The transcription factor p65 is involved in NF-κB heterodimer formation, with the phosphorylation of p65 being essential for NF-κB activation. MOLM-13 cells were seeded at 0.5 million cells per milliliter and subject to either 10 or 20 μM of DHL or PTL treatment for 6 hours. Cells were lysed and protein lysates were resolved on a 10% SDS-PAGE and transferred to PVDF membrane. The membrane was incubated with primary antibodies at 4° C. overnight, washed and incubated with IRDye 680 goat anti-rabbit or IRDye 800CW goat anti-mouse secondary antibodies at room temperature for 30 minutes. The membrane was then washed with phosphate buffered saline with 0.1% Tween 20x. The membrane was scanned using the Odyssey infrared imaging system. Phospho-NF-κB p65 mouse primary antibody and NF-κB p65 rabbit primary antibody were separately used to stain the membranes.

Strikingly, DHL and PTL both induced a significant decrease in phospho-p65. Total p65 is shown as a control. It is important to note that a similar change in phospho-p65 with DHL treatment was observed in in MV4-11 cells (Data not shown).

Example 6: Effects of Dehydroleucodine and its Derivatives on Gene Expression

MOLM-13 and KG-1 cells were seeded at 0.5 million cells per ml. Cells were treated for 6 hours with 20 μM of parthenolide (PTL), dehydroleucodine (DHL), leucodine (Leu), parthenolide-tyramine (PTL-Tyr), dehydroleucodine-tyramine (DHL-Tyr) and dehydroleucodine-Morpholine (DHL-Morp), and then collected. Total RNA was extracted using the Qiashredder and Qiagen Rneasy mini kits (Quiagen) according to the manufacturer's instructions. Real-time PCR was performed using the Taqman RNA to CT 1-Step kit (Applied Biosystems). The thermal cycling conditions were one RT step (48° C., 15 minutes), enzyme activation (95° C., 10 minutes) and 40 cycles of denature (95° C., 15 seconds) and anneal/extend (60° C., 1 minute). Real-time PCR was performed using probes for HMOX-1 (Hs01110251_m1), HSPA1A (Hs00359163_s1), or HSPH1 (Hs00971475_m1). GADPH (Hs02758991_g1) was used as an internal control to normalize the variability in expression levels. All probes were provided by Applied Biosystems. Single-plex real-time PCR was performed in triplicates in a StepOne plus Real-Time PCR system (Applied Biosystems) and analyzed with the StepOne Software. Fold change was calculated using the 2-DDCT method.

Figure 1E:
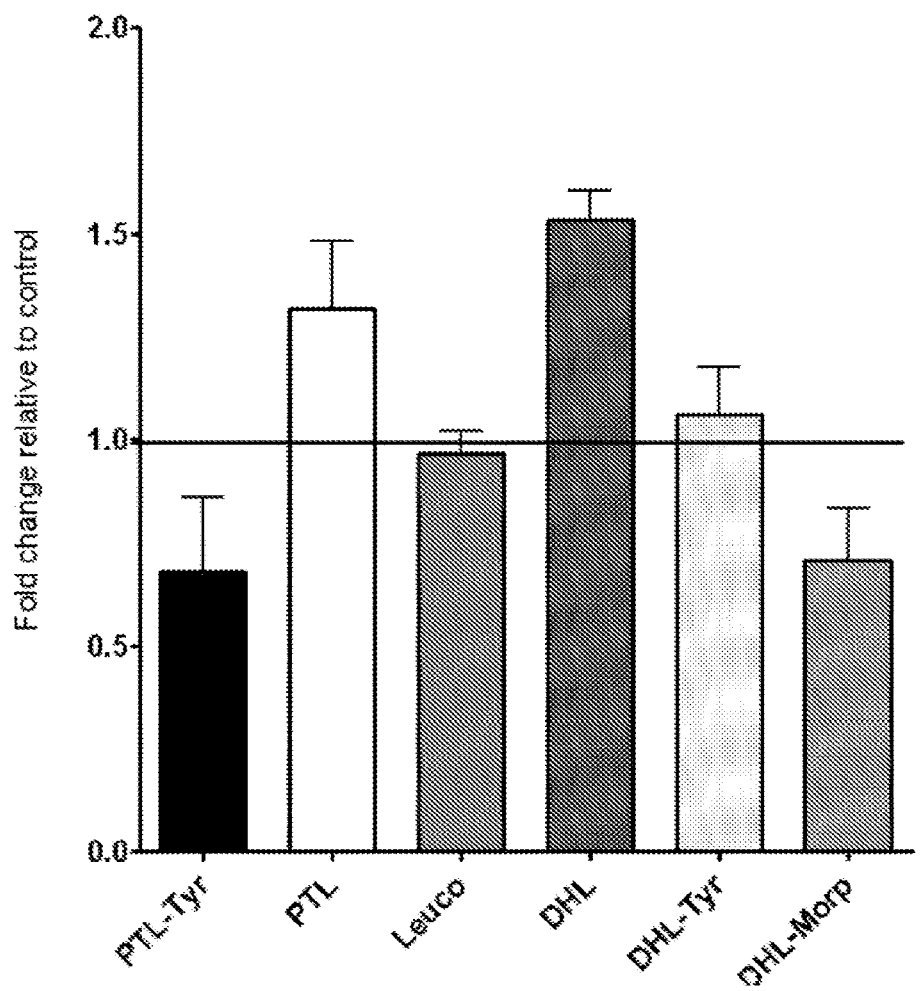

The changes in expression of HMOX-1, HSPA1A, and HSP1 in KG-1 cells are shown in FIGS. 1A, 1B, and 1C, respectively, and the changes in expression of HMOX-1 and HSP1 in MOLM-13 cells are presented in FIGS. 1D and 1E, respectively. DHL activated the expression of all three target genes in both cell lines, and DHL was more potent than PTL. Some of the DHL derivatives upregulated HSPH1 expression.

Example 7: Effects of Dehydroleucodine on Growth of Tumor Cells

As shown in Table 6, DHL inhibits tumor cells to varying degrees. DHL is cytotoxic to various leukemia, colon cancer, CNS cancer and prostate cancer cell lines. Surprisingly, DHL is not cytotoxic to various non-small cell lung cancer and ovarian cancer cell lines.

TABLE 6

Single dose results of dehydroleucodine tested at 10 μM

| Panel/Cell line | Percent inhibition |
| --- | --- |
| Panel cell lines for which DHL is cytotoxic | |
| Leukemia | |
| CCRF-CEM | 44.9 |
| K-562 | 42.0 |
| RPMI-8226 | 31.7 |
| Colon Cancer | |
| HCT-116 | 41.3 |
| SW-620 | 30.0 |
| CNS Cancer | |
| SNB-75 | 35.5 |
| U251 | 30.0 |

TABLE 6-continued

Single dose results of dehydroleucodine tested at 10 μM

| Panel/Cell line | Percent inhibition |
|---|---|
| Prostate Cancer | |
| PC-3 | 38.6 |
| DU-145 | 44.0 |
| Panel cell lines for which DHL is not cytotoxic | |
| Non-Small Cell Lung Cancer | |
| HOP-62 | 0.0 |
| NCI-H322M | 0.0 |
| NCI-H460 | 0.0 |
| Ovarian Cancer | |
| NCI/ADR-RES | 0.0 |
| SK-OV-3 | 0.0 |

What is claimed is:

1. A method for inhibiting growth of a blood cancer cell, wherein the cancer cell is a leukemic cell, the method comprising contacting the cancer cell with an effective amount of composition comprising a compound of Formula (Id), or a pharmaceutically acceptable salt thereof, wherein the composition is effective to inhibit growth of the cancer cell, wherein the compound comprises Formula (Id):

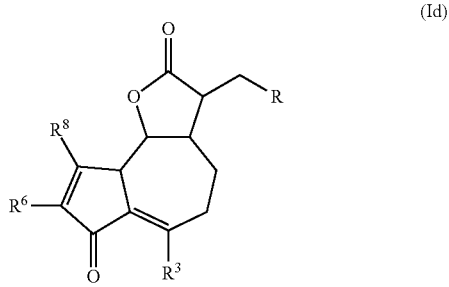

wherein:

R is proline; and $R^3$ is selected from hydrogen, $CH_3$, $CH_2OH$, $CH_2NH_2$, $CH_2Cl$, $CH_2Br$, $CH_2I$ or $CH_2F$;

$R^6$ is hydrogen; and $R^8$ is selected from hydrogen $CH_3$, $CH_2OH$, $CH_2NH_2$, $CH_2Cl$, $CH_2Br$, $CH_2I$ or $CH_2F$.

2. The method of claim 1, wherein the cancer cell is in vivo or in vitro.

3. The method of claim 1, wherein the inhibiting growth is measured as the expression of NF-κB.

4. The method of claim 1, wherein the inhibiting growth is measured as the expression of markers of oxidative stress.

5. The method of claim 4, wherein the markers of oxidative stress are selected from the group consisting of HMOX1, HSPA1A and HSPH1.

6. The method of claim 1, wherein the leukemic cell is an acute myeloid leukemia cell, a chronic myeloid leukemia cell, an acute lymphocytic leukemia cell, a chronic lymphocytic leukemia cell, or a cutaneous T cell leukemia.

7. The method of claim 2, wherein the blood cancer cell is disposed in a subject and the blood cancer cell is contacted by administering the composition comprising a compound of Formula (Id) to the subject.

8. The method of claim 7, wherein the subject has or is suspected of having acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia.

9. The method of claim 1, wherein the composition comprising a compound of Formula (Id) selectively inhibits growth of cancer cells and does not appreciably kill non-cancer cells at the same concentration.

* * * * *